US012678140B2

(12) United States Patent
Taniguchi

(10) Patent No.: US 12,678,140 B2
(45) Date of Patent: Jul. 14, 2026

(54) DIAGNOSTIC ULTRASOUND APPARATUS AND STORAGE MEDIUM

(71) Applicant: Konica Minolta, Inc., Tokyo (JP)

(72) Inventor: Tetsuya Taniguchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 403 days.

(21) Appl. No.: 17/822,012

(22) Filed: Aug. 24, 2022

(65) Prior Publication Data

US 2023/0065358 A1 Mar. 2, 2023

(30) Foreign Application Priority Data

Sep. 2, 2021 (JP) ................................. 2021-142891

(51) Int. Cl.
 *A61B 8/00* (2006.01)
 *G01S 7/52* (2006.01)
 *G01S 15/89* (2006.01)

(52) U.S. Cl.
 CPC ........ *A61B 8/5207* (2013.01); *G01S 7/52026* (2013.01); *G01S 7/52038* (2013.01); *G01S 15/8977* (2013.01)

(58) Field of Classification Search
 CPC ............... A61B 8/5207; G01S 15/8977; G01S 15/8995; G01S 7/52026; G01S 7/52031; G01S 7/52038; G01S 7/52046; G01S 7/52049
 See application file for complete search history.

(56) References Cited

U.S. PATENT DOCUMENTS

| | | | | |
|---|---|---|---|---|
| 5,961,460 | A | * | 10/1999 | Guracar ................... A61B 8/14 600/458 |
| 2004/0054285 | A1 | * | 3/2004 | Freiburger .......... G01S 7/52046 600/447 |
| 2005/0053308 | A1 | * | 3/2005 | Sabourin ............. G01S 15/8979 382/284 |
| 2010/0312112 | A1 | * | 12/2010 | Kamiyama .............. A61B 8/14 600/443 |

(Continued)

FOREIGN PATENT DOCUMENTS

| | | |
|---|---|---|
| JP | 2004-522515 A | 7/2004 |
| JP | 2006-051229 A | 2/2006 |

(Continued)

OTHER PUBLICATIONS

Guruprasad, Prathima. "Overview of different thresholding methods in image processing." TEQIP sponsored 3rd national conference on ETACC. 2020.*

(Continued)

*Primary Examiner* — Carolyn A Pehlke

(74) *Attorney, Agent, or Firm* — LUCAS & MERCANTI, LLP

(57) ABSTRACT

A diagnostic ultrasound apparatus includes: a sound ray signal generator that generates a sound ray signal based on a reception signal obtained from an ultrasound probe that transmits and receives ultrasound to and from a subject; an imaging signal generator that performs filtering of passing different bands on the sound ray signal to generate multiple imaging signals from the sound ray signal; and a calculator that performs an arithmetic operation among the imaging signals.

11 Claims, 22 Drawing Sheets

(56)     References Cited

U.S. PATENT DOCUMENTS

2013/0258805  A1 *  10/2013  Hansen ................... G01S 15/89
                                                                    367/8
2018/0116631  A1 *   5/2018  Taniguchi ............ A61B 8/5215
2023/0066202  A1 *   3/2023  Xia ..................... G01S 7/52046

FOREIGN PATENT DOCUMENTS

JP          2006-204594  A       8/2006
JP          2009-039284  A       2/2009
JP           2017121413  A   *   7/2017

OTHER PUBLICATIONS

Wilhjelm, Jens E., et al. "Visual and quantitative evaluation of selected image combination schemes in ultrasound spatial compound scanning." IEEE transactions on medical imaging 23.2 (2004): 181-190.*
Hiroshi Akima, et al., "Relationship between quadriceps echo intensity and functional and morphological characteristics in older men and women," Archives of Gerontology and Geriatrics, vol. 70, pp. 105-111, 2017.
Office Action, dated Mar. 4, 2025, issued for the corresponding Japanese Patent Application No. 2021-142891, 8 pages, with English translation.

* cited by examiner

FIG. 2

TRANSMISSION WAVE                     RECEPTION WAVE

TRANSMISSION WAVE

RECEPTION WAVE

COMBINED

OFFSET

OFFSET

OUTPUT SIGNAL [%]

INPUT SIGNAL [%]

I15

I35

I25

I45

RATIO OF DARK (BLACK) PIXELS IN
ULTRASOUND IMAGE REGION IN I25 = 18%

RATIO OF DARK (BLACK) PIXELS IN
ULTRASOUND IMAGE REGION IN I45 = 19%

DIAGNOSTIC ULTRASOUND APPARATUS AND STORAGE MEDIUM

CROSS-REFERENCE TO RELATED APPLICATIONS

The entire disclosure of Japanese Patent Application No. 2021-142891 filed on Sep. 2, 2021 is incorporated herein by reference in its entirety.

BACKGROUND

Technological Field

The present disclosure relates to a diagnostic ultrasound apparatus and a storage medium.

Description of Related Art

In ultrasonography, ultrasound images showing the state of the heart or a fetus can be obtained by simply applying an ultrasound probe to the body surface or the body cavity of a subject of a patient. Ultrasonography is safe and therefore allows repetitive examinations. A diagnostic ultrasound apparatus used for ultrasonography is known.

In general, an ultrasound image indistinguishably displays echo signal components of reflected ultrasound (echo) reflected by structures larger than the ultrasound wavelength and echo signal components scattered by structures smaller than the ultrasound wavelength. Reflector echo signals by reflectors larger than the ultrasound wavelength are signals corresponding to the morphologies/structures of the reflectors and obtained as the morphologies thereof directly. In contrast, scatterer echo signals by scatterers smaller than the ultrasound wavelength do not directly reflect morphologies of the scatterers because they are smaller than the ultrasound wavelength.

The scatterer echo signals are results of scattering and interference derived from tissues. In parenchymal regions, such as liver and thyroid gland, the scatterer echo signals are observed as so-called speckles, and their uniformity, granularity, and so forth are utilized as diagnostic information.

Normally, the inside of a skeletal muscle of a young individual mainly consists of muscular tissues, and acoustic scattering does not occur often. Regarding an old individual, on the other hand, it is known that adipose tissues may enter into the skeletal muscle and cause acoustic scattering, which increases brightness of muscles (non-patent document 1: Relationship between quadriceps echo intensity and functional and morphological characteristics in older men and women (Archives of Gerontology and Geriatrics, 2017 Jan. 24, electronic edition)).

There is also known a technique for obtaining an aimed ultrasound image by adding up ultrasound images. For example, JP 2006-51229A discloses an image processing apparatus that calculates a weighting coefficient according to pixel value change information that indicates a larger absolute value for a larger spatial change of sampling data obtained by a diagnostic ultrasound apparatus; and adds up the sampling data and a smoothed image of the sampling data by using the weighting coefficient. This image processing apparatus certainly removes or reduces image noise mainly of high-frequency components, ensures information on regions that are important in observation and that contain many high-frequency components (e.g., boundaries of structures on the image), and reduces speckle noise.

Further, JP 2006-204594A discloses a diagnostic ultrasound apparatus that extracts frequency components from a reception signal obtained by receiving ultrasound, generates multiple types of image data based on intensity changes of the frequency components, performs spatial filtering on at least one type of the image data, and combines the multiple types of the image data. On the basis of this combined image data, the diagnostic ultrasound apparatus highlights a tissue of a living body by utilizing difference in frequency pass characteristics of tissues of a living body.

Further, JP2009-39284A discloses an ultrasound imaging apparatus that raises a reception echo signal that has the center frequency of nf1 (n: natural number) to the power of (n+1); raises a reception echo signal that ha the center frequency of (n+1)f1 to the power of n; and obtains signals that have the center frequency of n(n+1)f1. By performing phase-sensitive detection on the obtained signals, the ultrasound imaging apparatus obtains signed echo signals corresponding to the interface where the acoustic impedance increases and corresponding to the interface where the acoustic impedance decreases.

SUMMARY

Noise (scattered acoustic noise), such as speckles caused by scatter components, is required to be removed from ultrasound images of the subject. As described in the non-patent document 1, due to the change in tissues and scatter components, the ultrasound image of an old individual delineates images less conspicuously as compared with the ultrasound image of a young individual. As a result, in puncturing a part of the skeletal muscle or the neck, a target tissue and/or a puncture needle are less visible. This makes it difficult to perform safe and accurate punctuation.

According to JP2006-51229A, although the image processing apparatus can retain the resolution around the edges of structures having large signal intensity (e.g., the periphery of an organ), the apparatus may not retain the resolution of tissue structures where signal intensity difference is small (e.g., fine structure inside an organ or tumor) because these small structures are smoothed together with speckles.

According to JP2006-204594A, although the diagnostic ultrasound apparatus can obtain information based on differences in frequency characteristics of tissues, the apparatus naturally generates an image based on signals of a narrow band centering on the selected frequency. The apparatus is therefore unable to achieve a high resolution.

Further, according to JP2009-39284A, the ultrasound imaging apparatus may not remove scattered acoustic noise by raising the same reception signals (reception echo signals) to the power of n.

An object of the present invention is to achieve both the high resolution and visibility of tissues for a subject that contains scatterers in tissues by depicting echo components of the tissues (reflectors) based on the reflection of ultrasound and by suppressing scattering acoustic noise caused by high-frequency ultrasound signals that are susceptible to scattering.

To achieve the above object, according to an aspect of the present invention, a diagnostic ultrasound apparatus includes: a sound ray signal generator that generates a sound ray signal based on a reception signal obtained from an ultrasound probe that transmits and receives ultrasound to and from a subject; an imaging signal generator that performs filtering of passing different bands on the sound ray signal to generate multiple imaging signals from the sound ray signal; and a calculator that performs an arithmetic operation among the imaging signals.

According to another aspect of the present invention, a diagnostic ultrasound apparatus includes: a sound ray signal generator that performs phasing and summing of a reception signal according to different phase-and-sum conditions to generate multiple sound ray signals, the reception signal being obtained from an ultrasound probe that transmits and receives ultrasound to and from a subject; and a calculator that performs an arithmetic operation among imaging signals that are based on the sound ray signals.

According to another aspect of the present invention, a non-transitory computer-readable storage medium stores a program that causes a computer to function as: a sound ray signal generator that generates a sound ray signal based on a reception signal obtained from an ultrasound probe that transmits and receives ultrasound to and from a subject; an imaging signal generator that performs filtering of passing different bands on the sound ray signal to generate multiple imaging signals from the sound ray signal; and a calculator that performs an arithmetic operation among the imaging signals.

According to another aspect of the present invention, a non-transitory computer-readable storage medium stores a program that causes a computer to function as: a sound ray signal generator that performs phasing and summing of a reception signal according to different phase-and-sum conditions to generate multiple sound ray signals, the reception signal being obtained from an ultrasound probe that transmits and receives ultrasound to and from a subject; and a calculator that performs an arithmetic operation among imaging signals that are based on the sound ray signals.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

Figure 2:
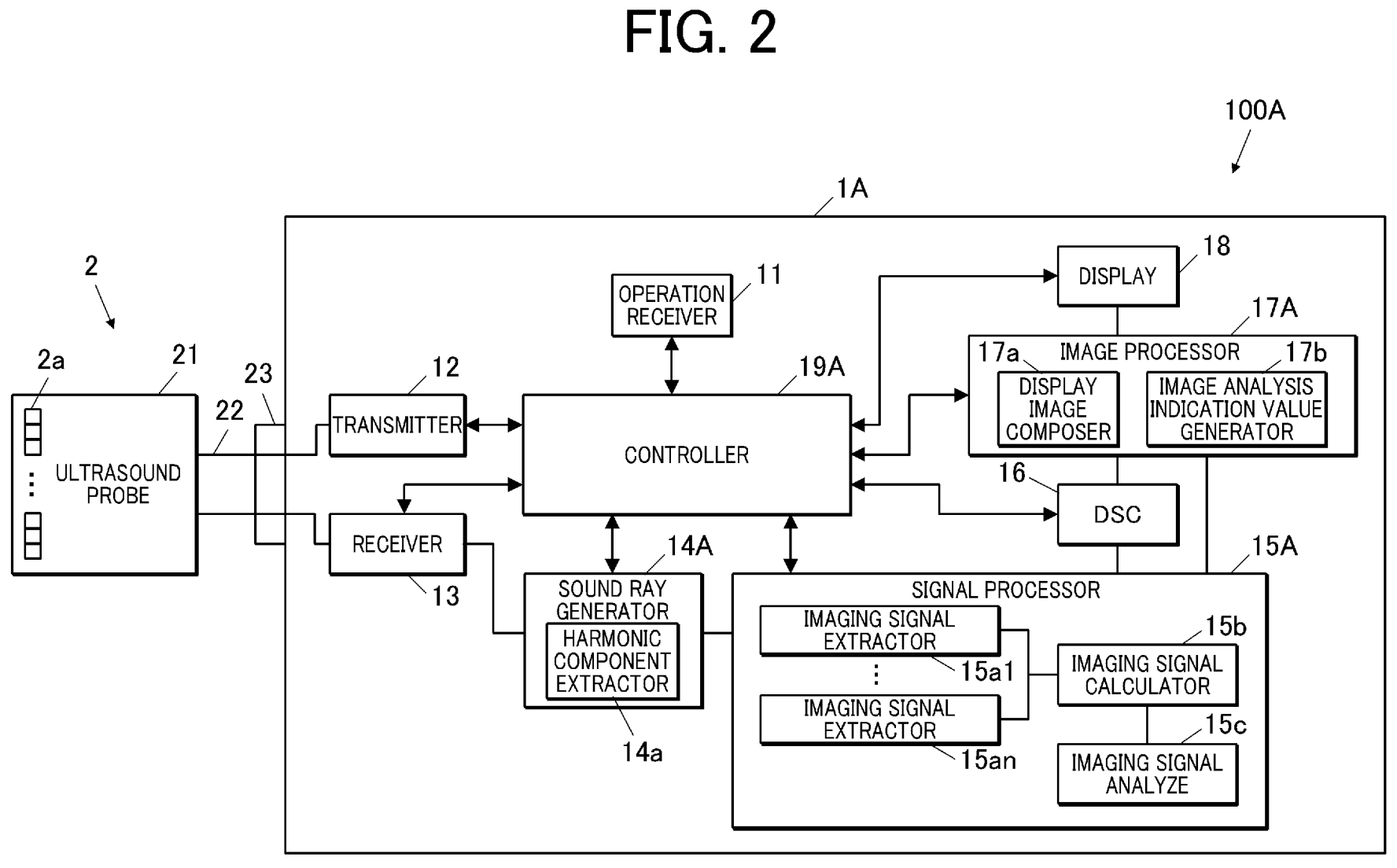

FIG. 2 is a block diagram showing functional components of the diagnostic ultrasound apparatus in the first embodiment;

4

Figure 10A:
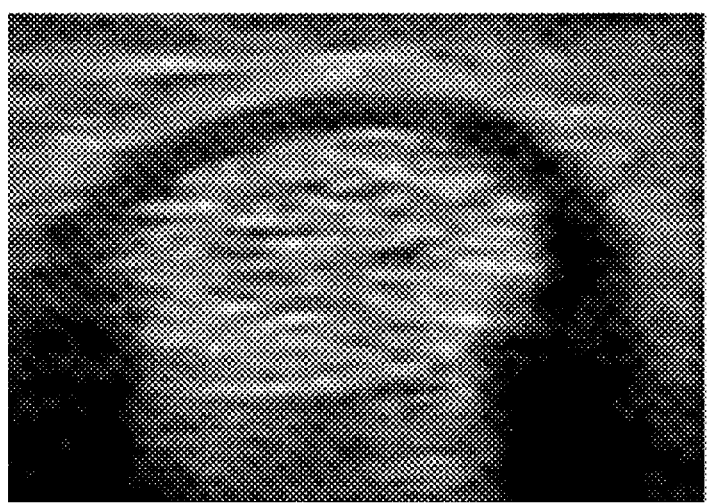
Figure 10B:
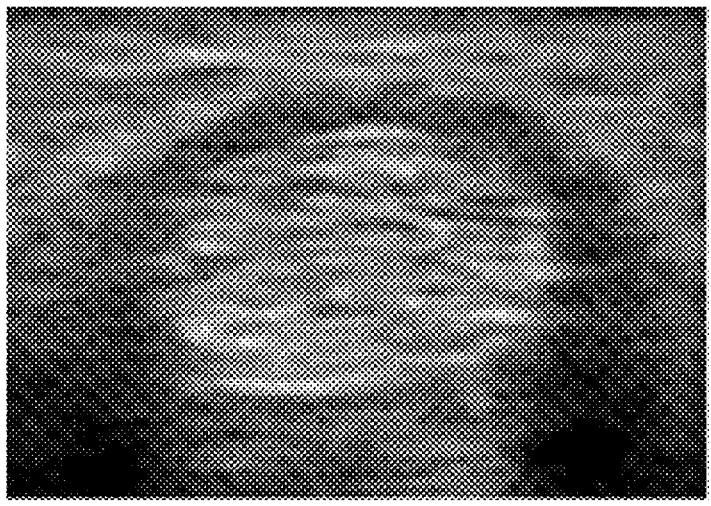
Figure 11:
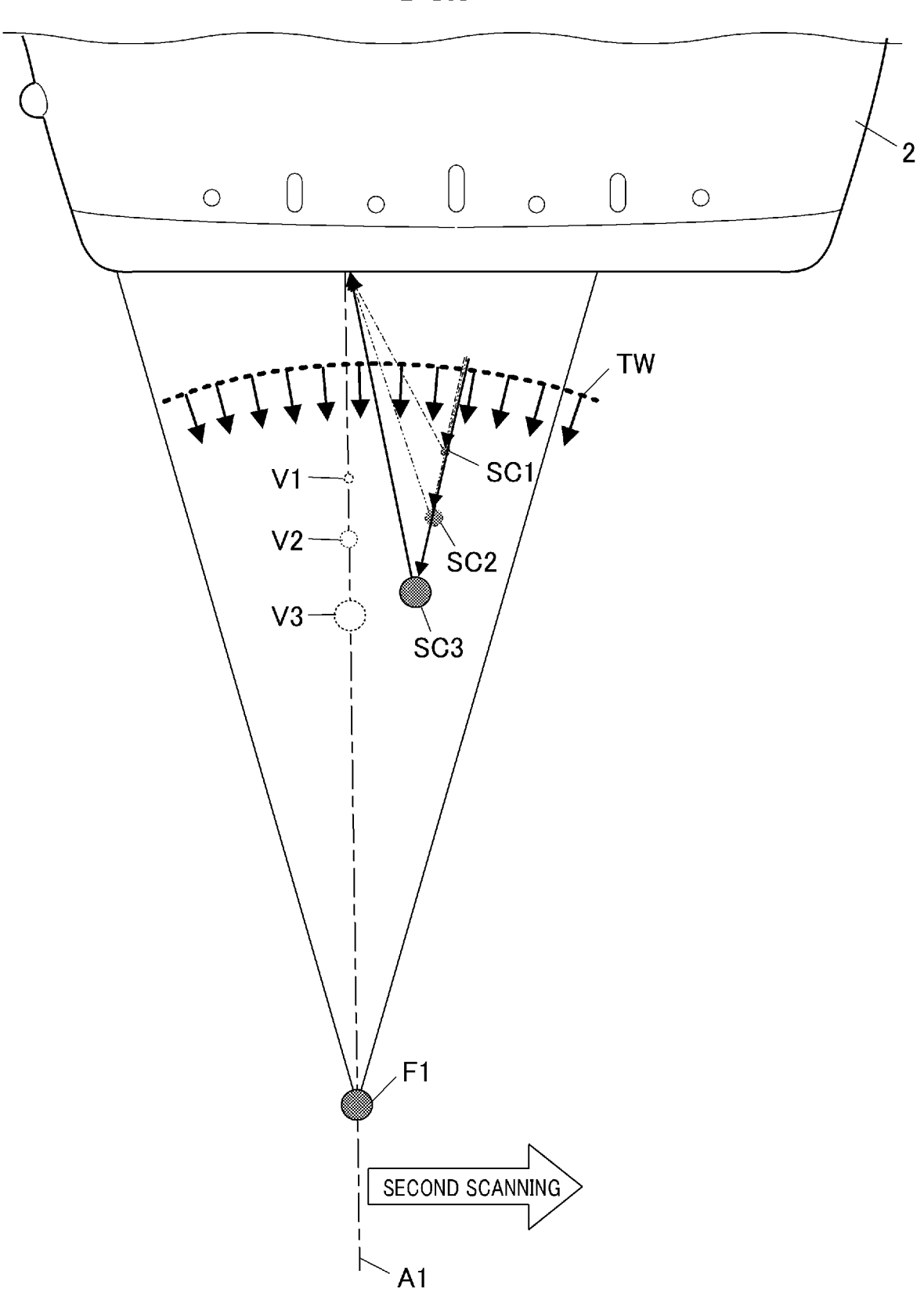
Figure 12:
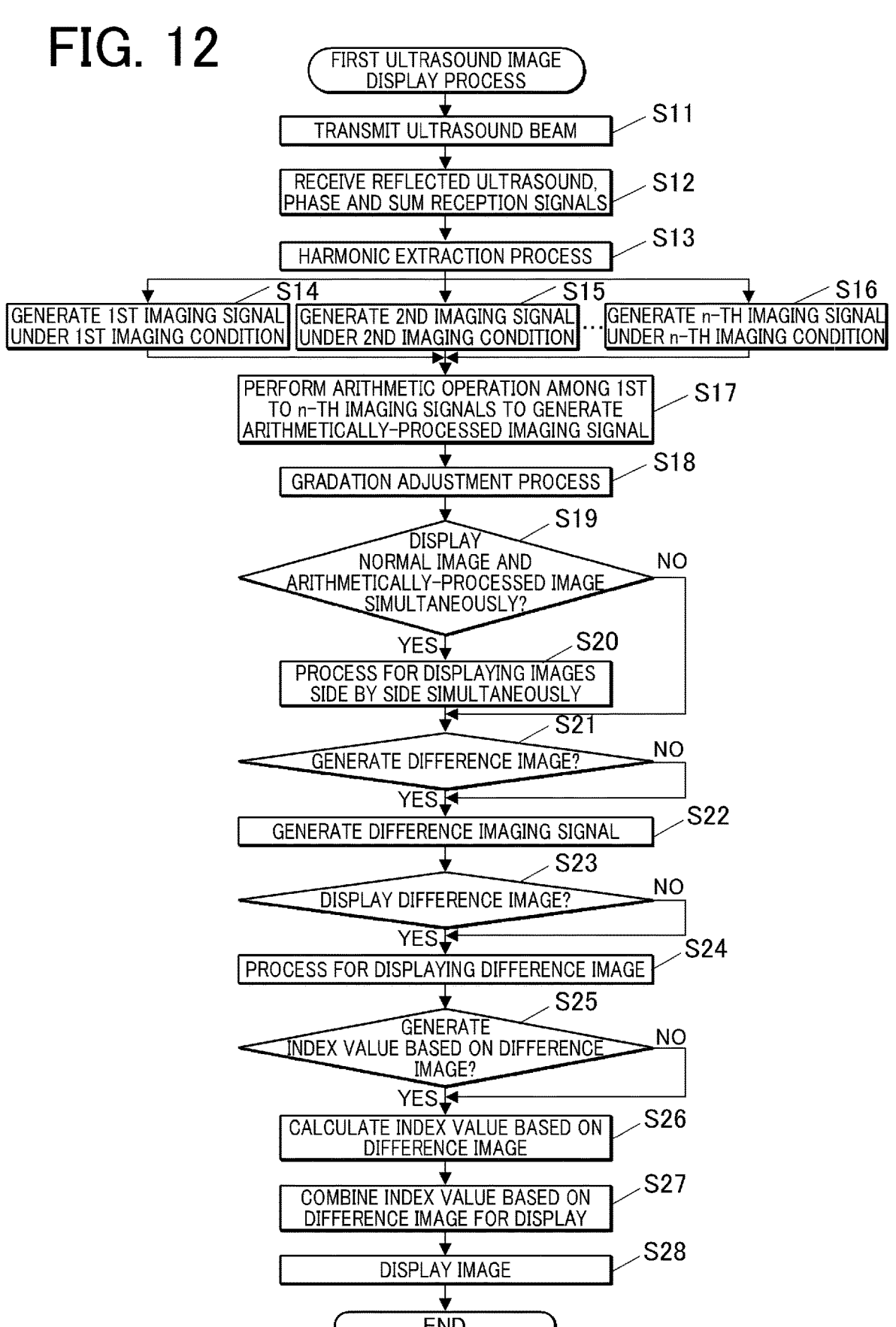
Figure 13:
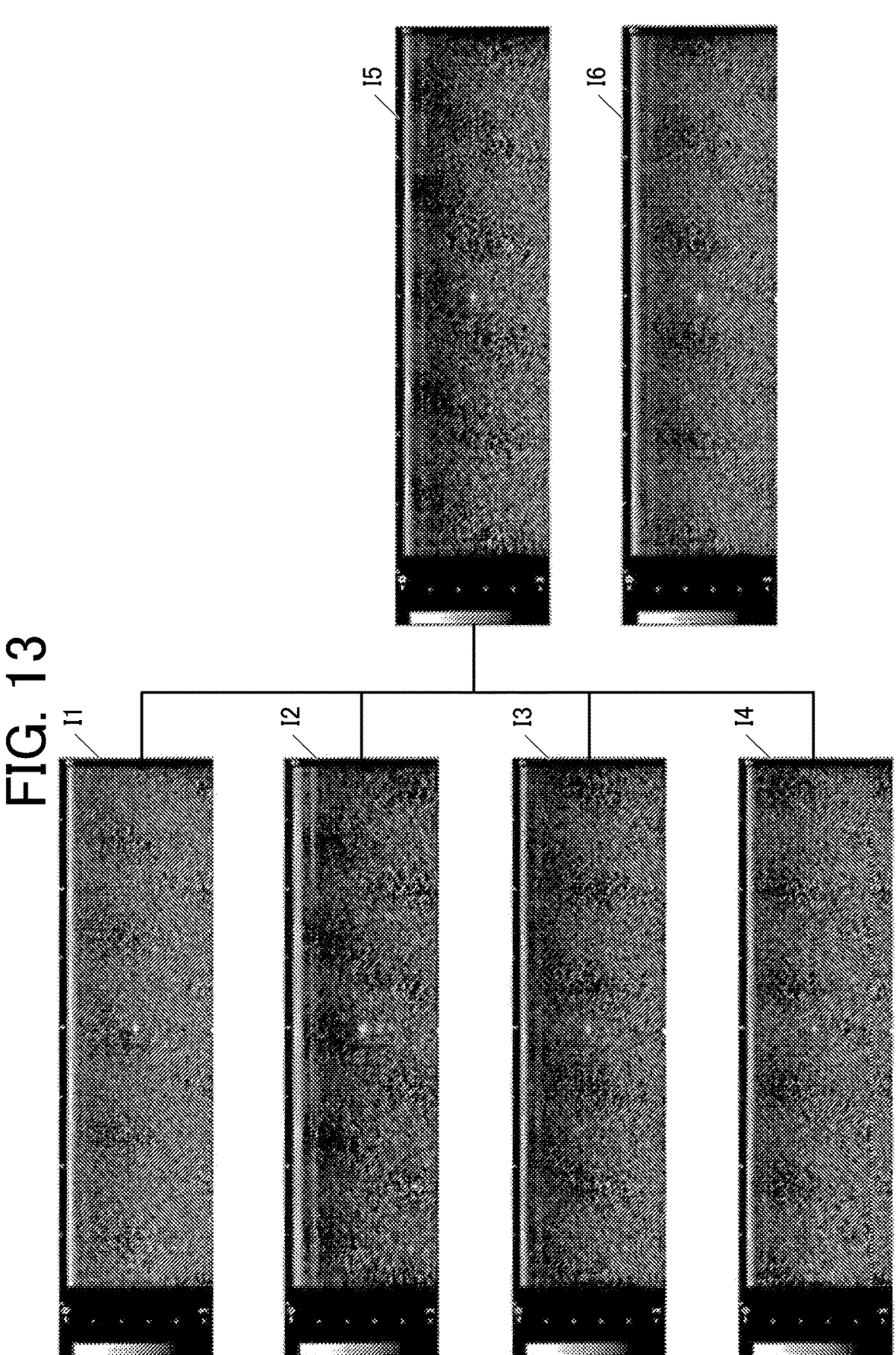
Figure 14A:
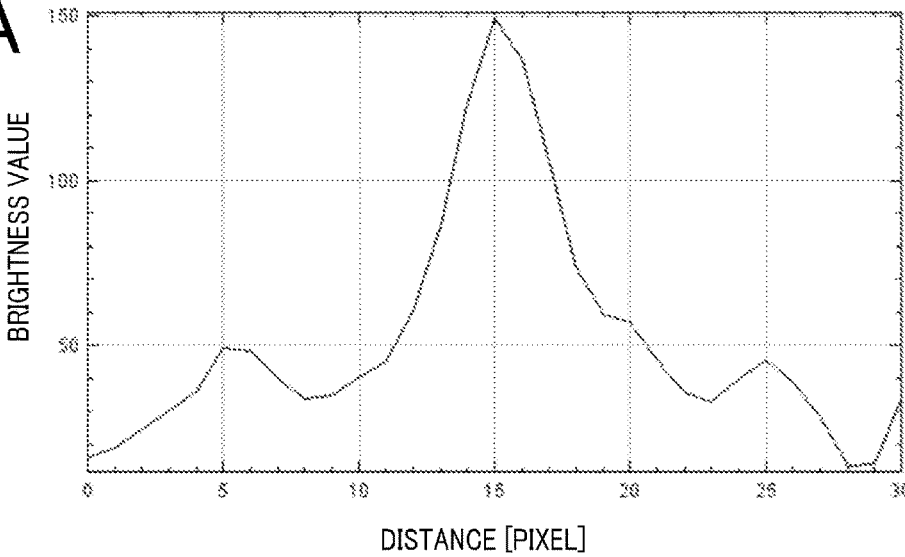
Figure 14B:
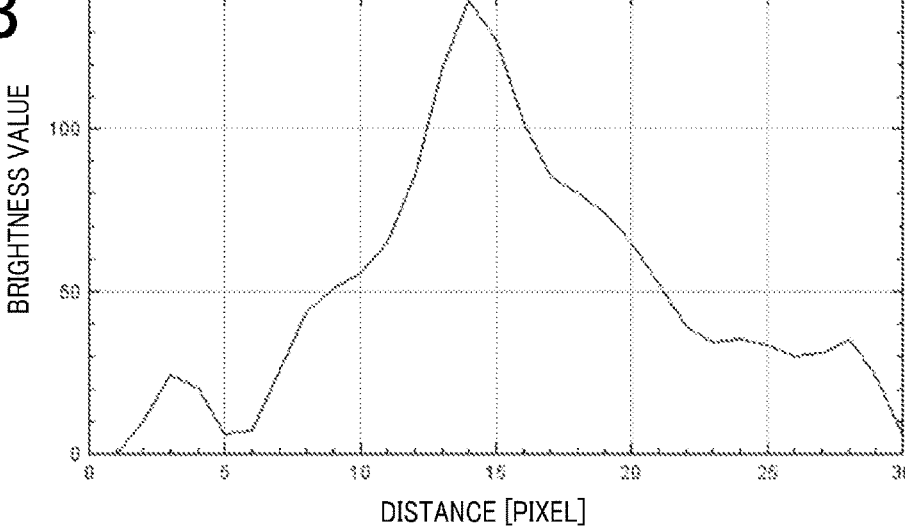
Figure 14C:
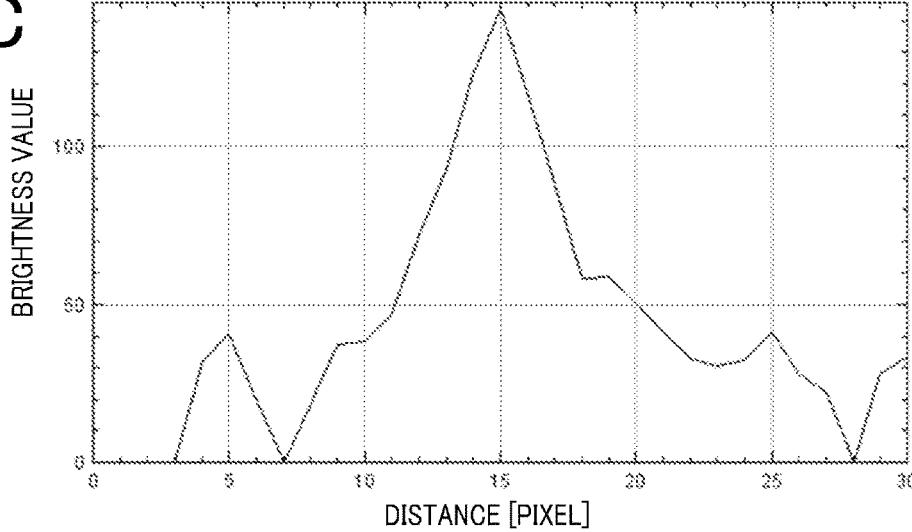
Figure 15:
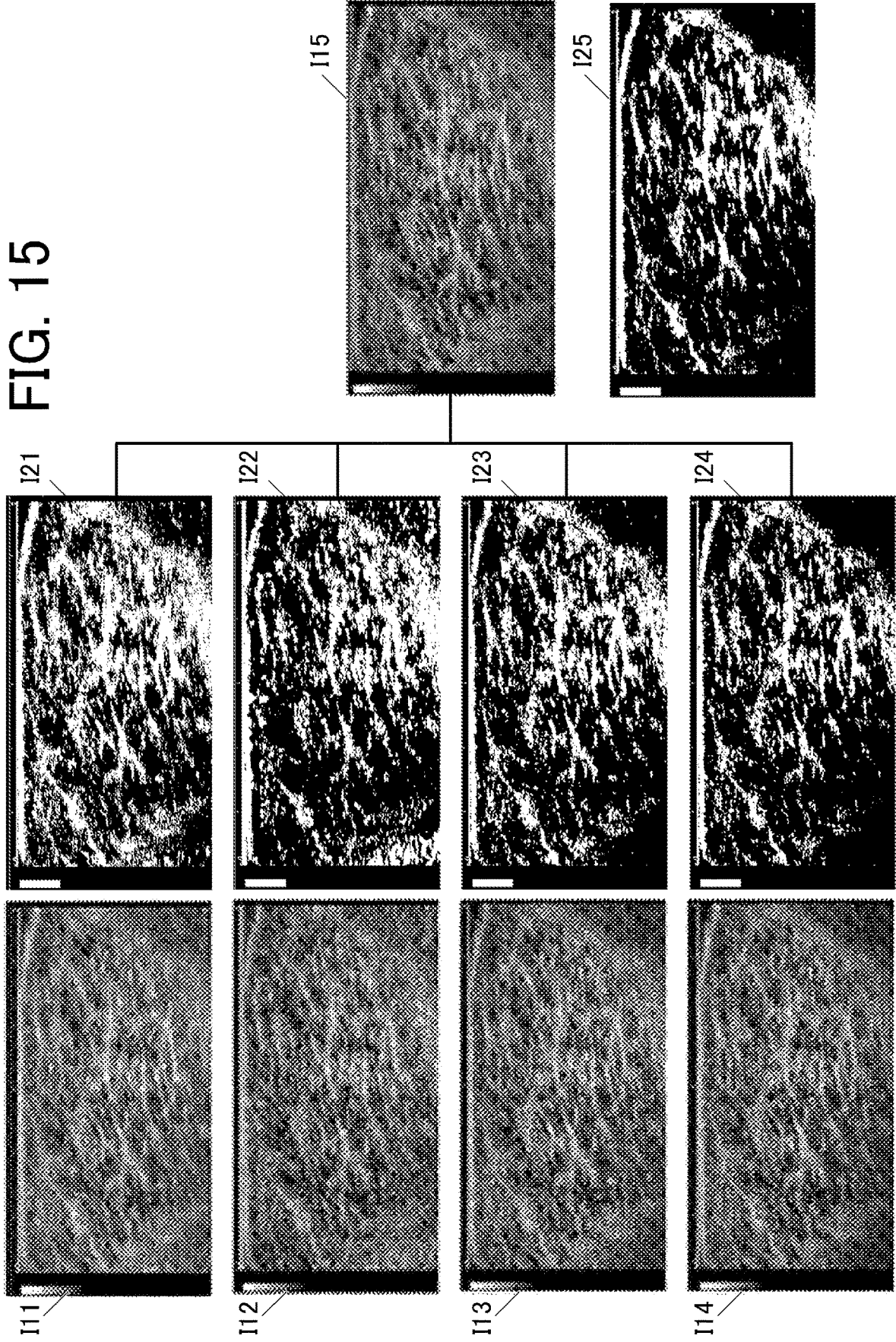
Figures 16, 17:
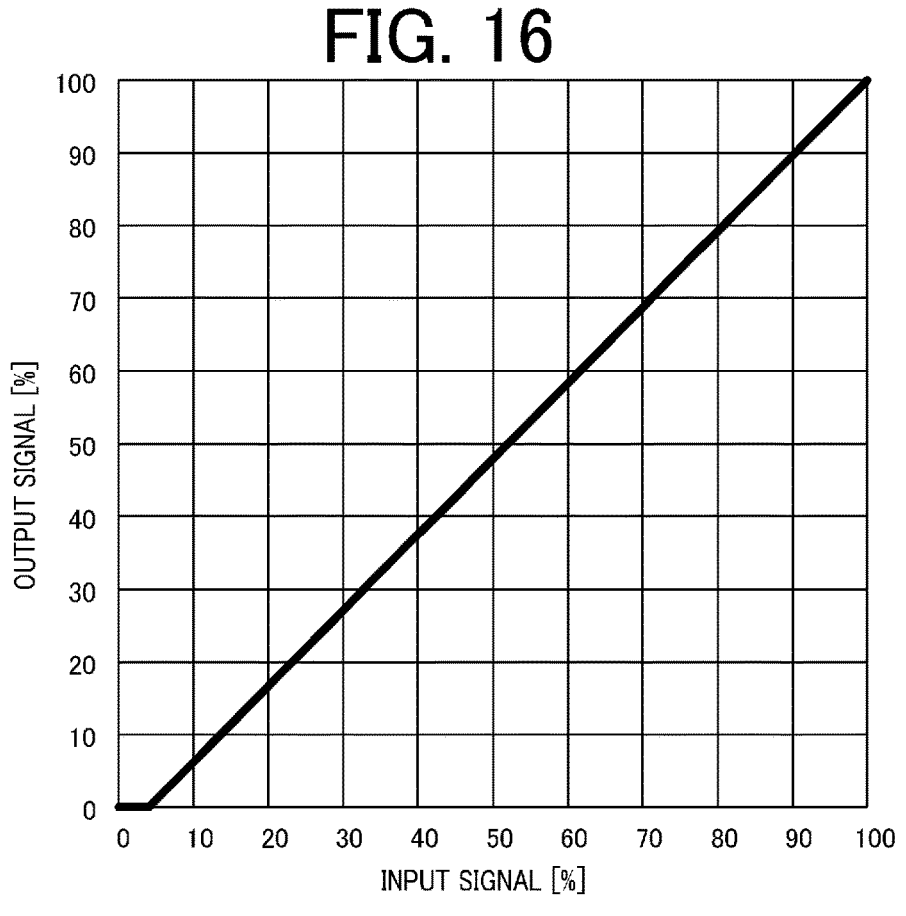
Figure 18:
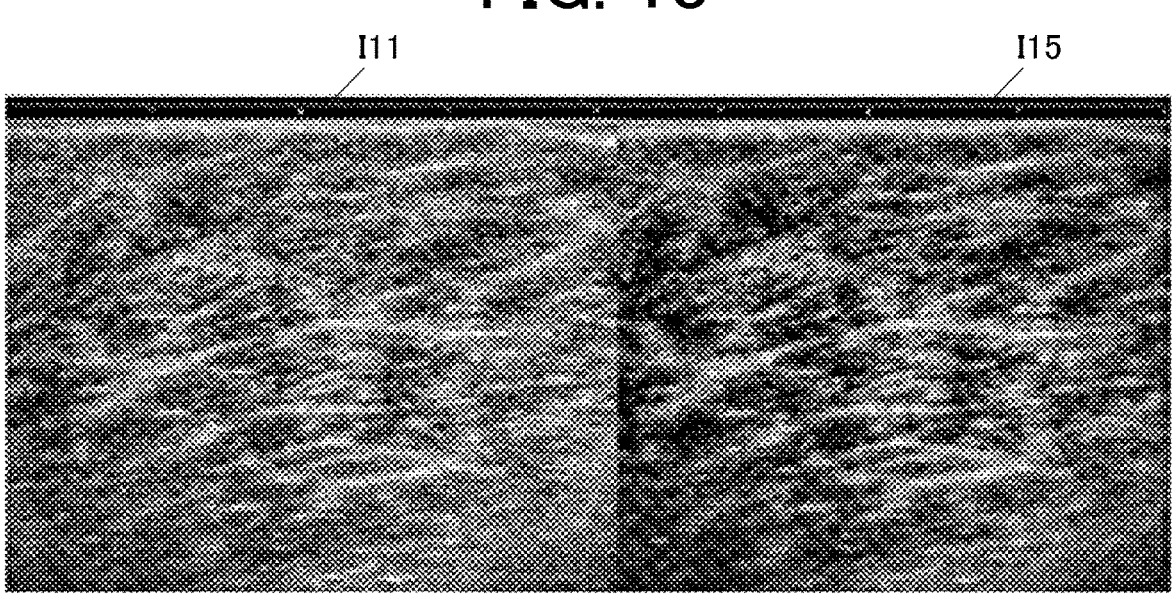
Figure 19:
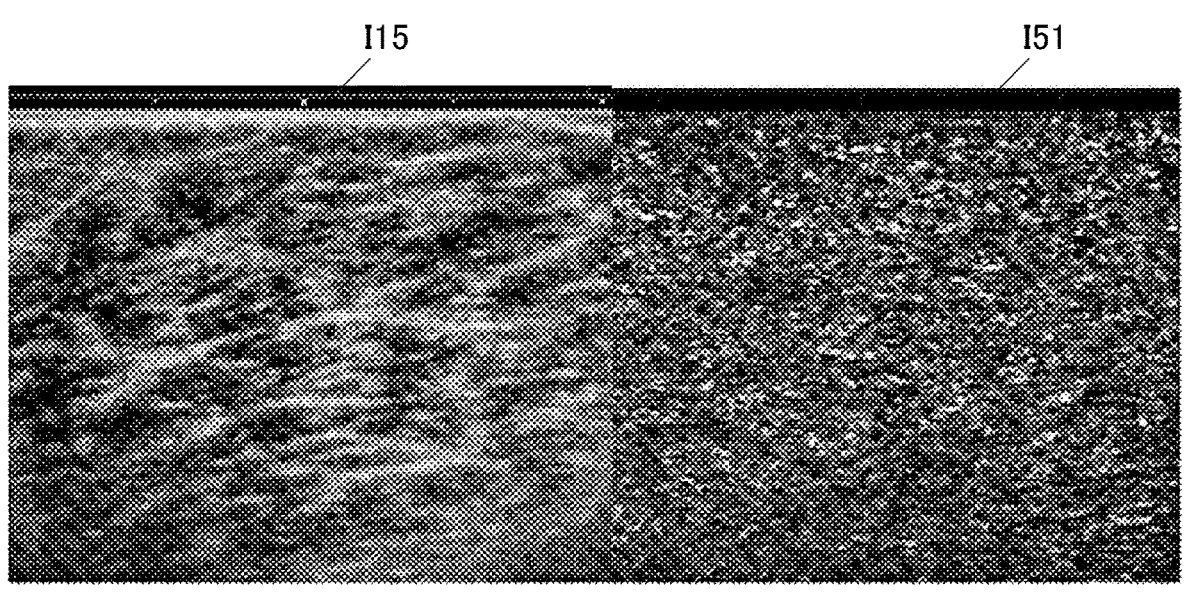
Figure 21:
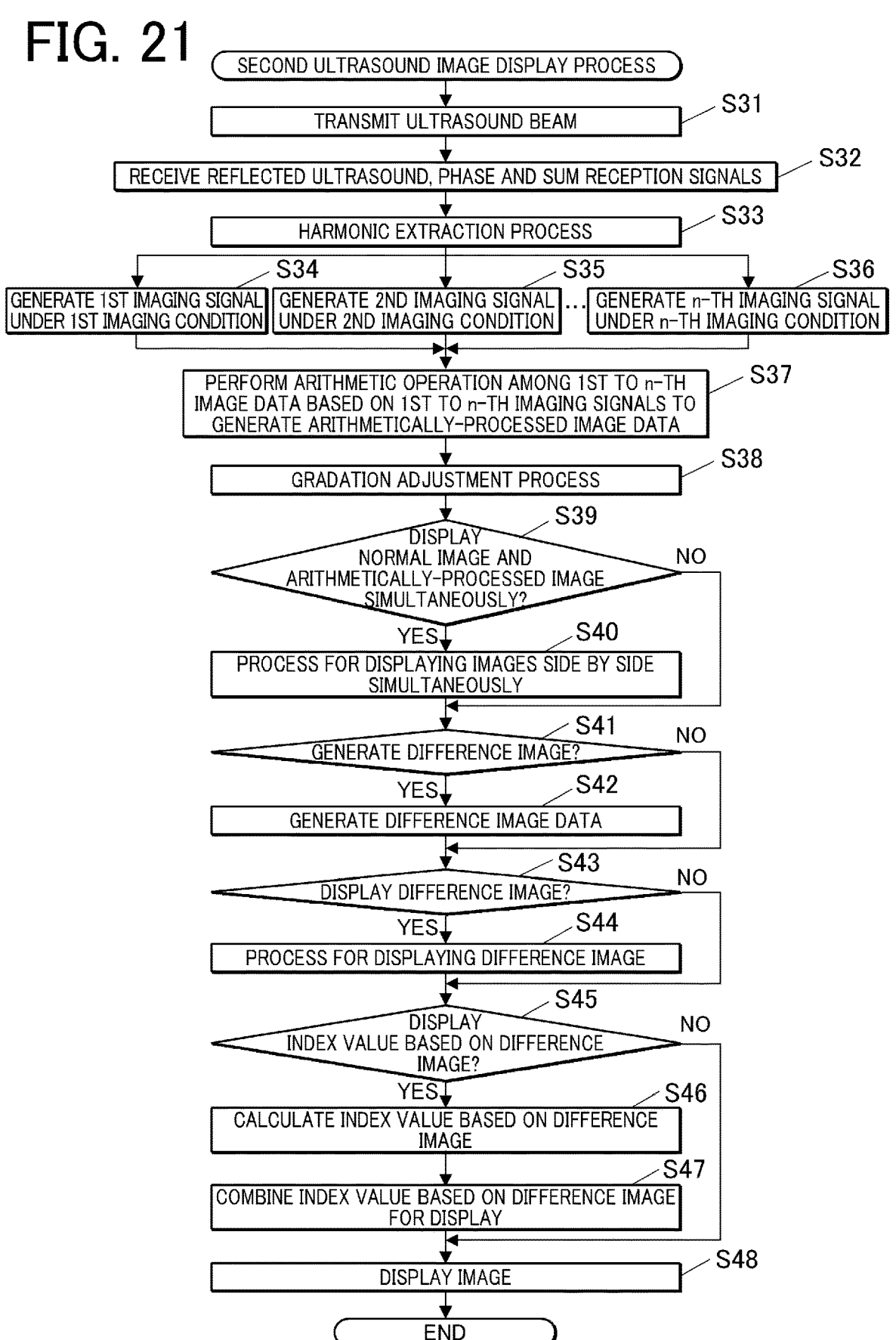
Figure 23:
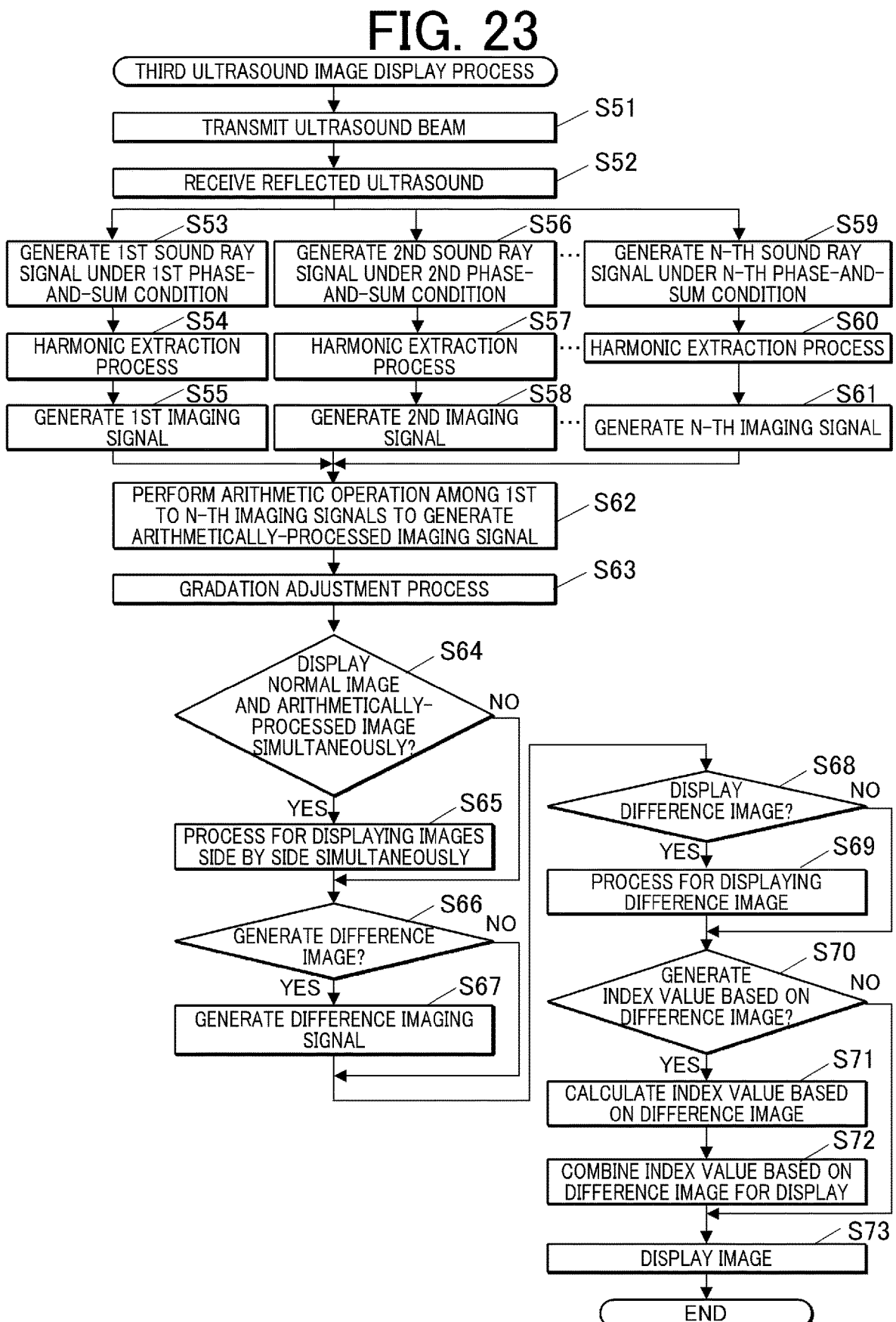
Figure 25:
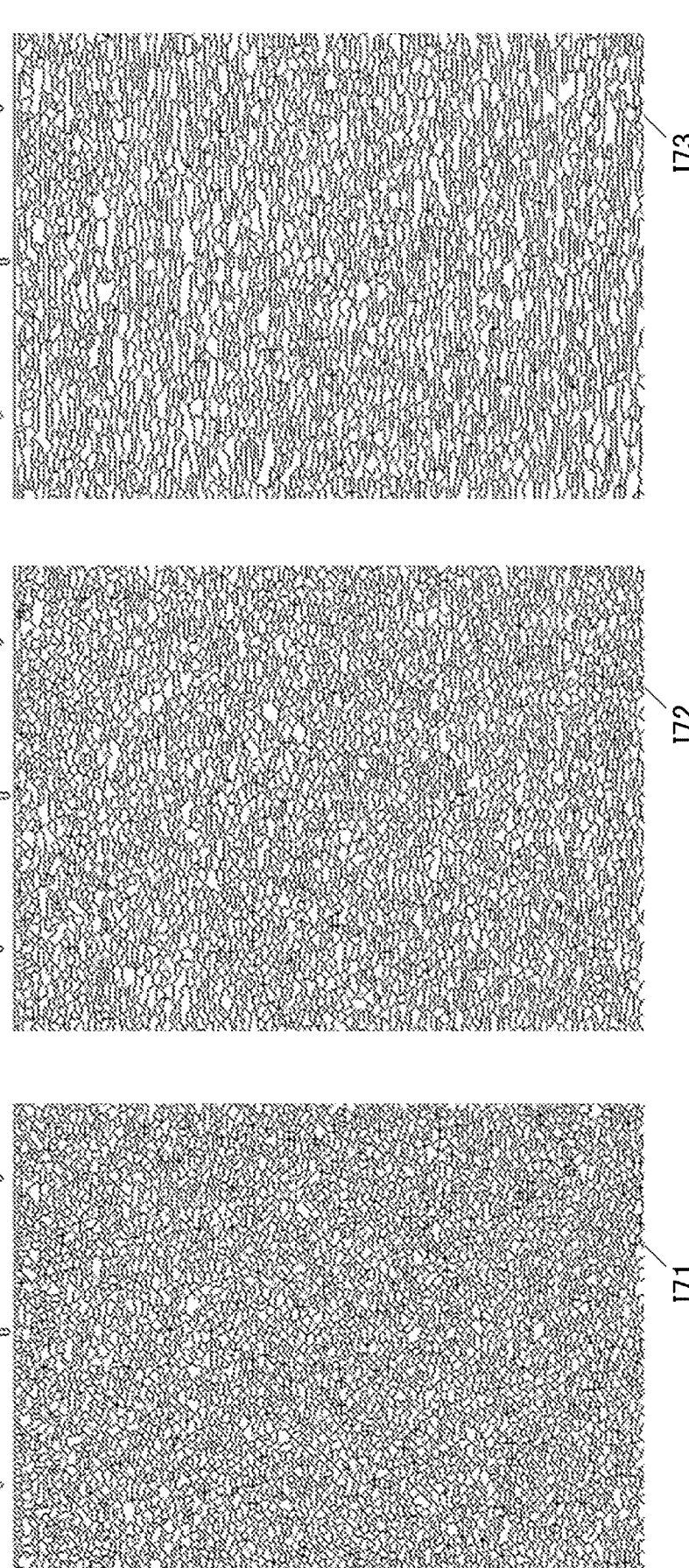
Figure 26:
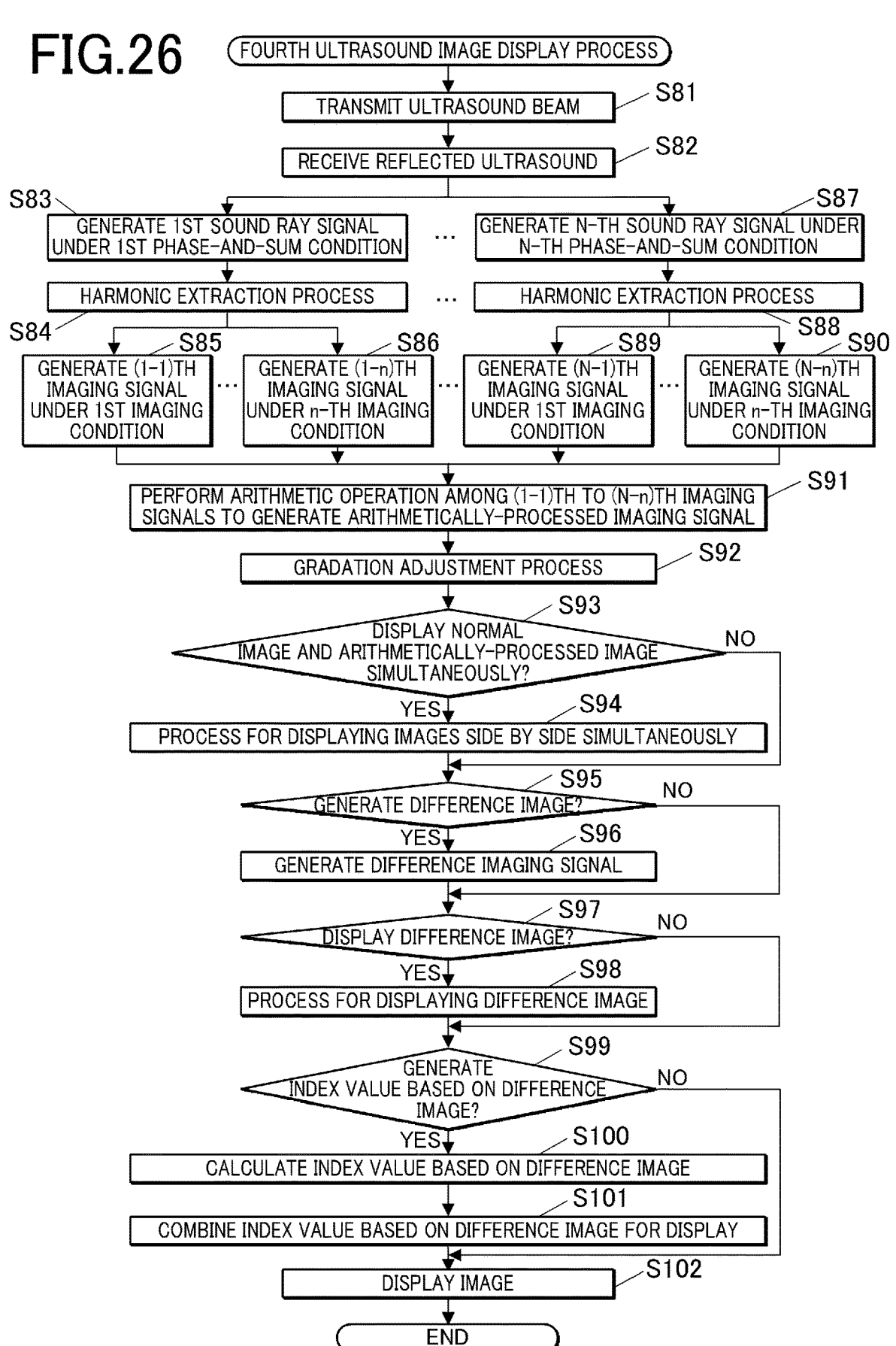

FIG. 10A shows an example of an ultrasound image with less scattering virtual images;

FIG. 10B shows an example of an ultrasound image with more scattering virtual images;

FIG. 11 shows the ultrasound probe, scatter sources, and virtual images of the scatter sources;

FIG. 12 is a flowchart of a first ultrasound-image display process;

FIG. 13 shows ultrasound images, an arithmetically-processed image, and a simple average image;

FIG. 14A shows pixel values of a predetermined distance including the highest brightness point of a wire target in one of the ultrasound images shown in FIG. 13;

FIG. 14B shows pixel values of the predetermined distance including the highest brightness point of the wire target in one of the ultrasound images shown in FIG. 13;

FIG. 14C shows pixel values of the predetermined distance including the highest brightness point of the wire target in the arithmetically-processed image shown in FIG. 13;

FIG. 15 shows ultrasound images, binarized images, an arithmetically-processed image, and a binarized arithmetically-processed image;

FIG. 16 shows an example of a look up table (LUT);

FIG. 17 shows the arithmetically-processed image and the binarized arithmetically-processed image shown in FIG. 15 and the arithmetically-processed image and the binarized arithmetically-processed image after LUT conversion;

FIG. 18 shows side-by-side display of the ultrasound image and the arithmetically-processed image shown in FIG. 4;

FIG. 19 shows side-by-side display of the arithmetically-processed image shown in FIG. 4 and a difference image;

Figure 20:
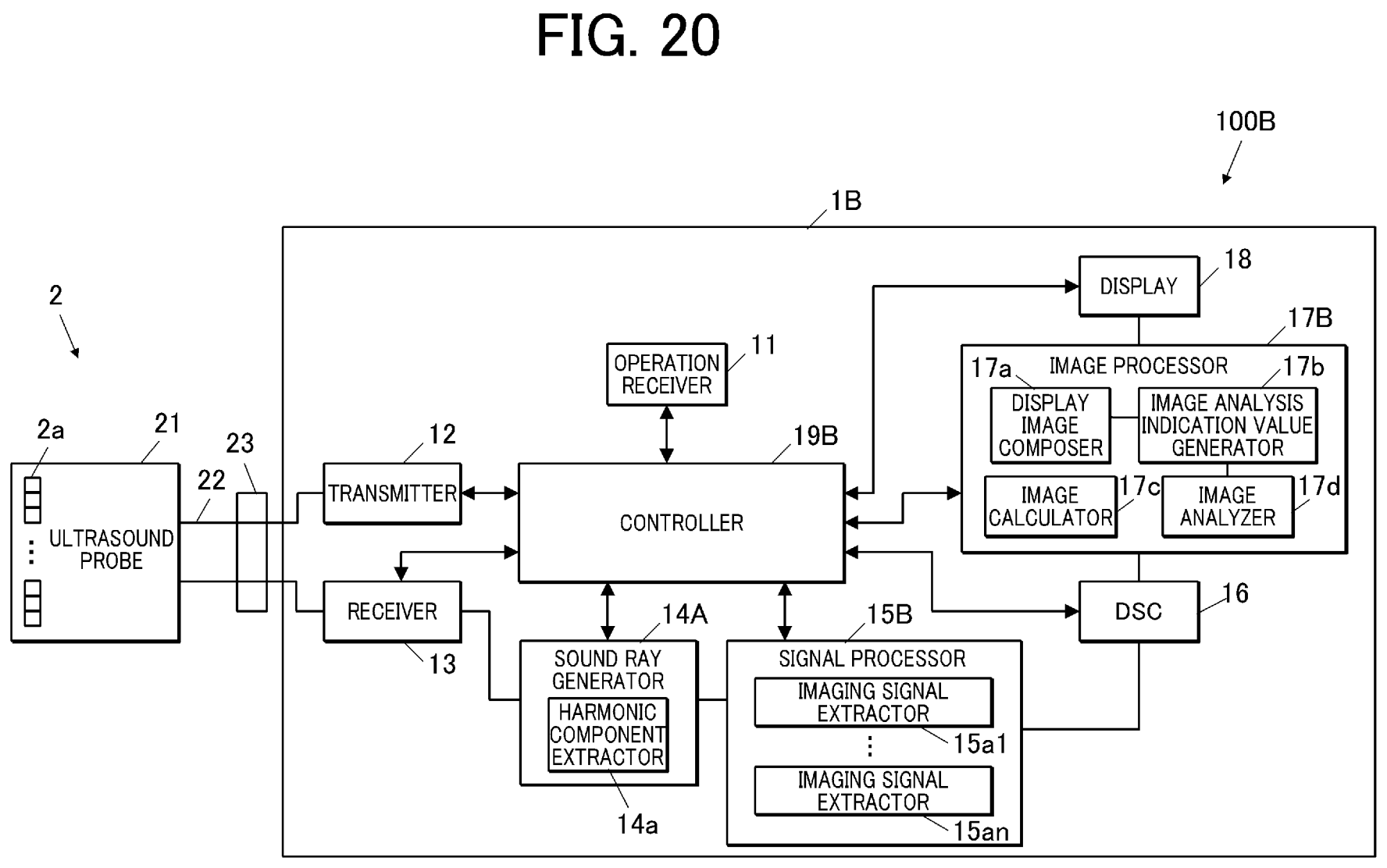

FIG. 20 is a block diagram showing functional components of the diagnostic ultrasound apparatus in a second embodiment;

FIG. 21 is a flowchart of a second ultrasound-image display process;

Figure 22:
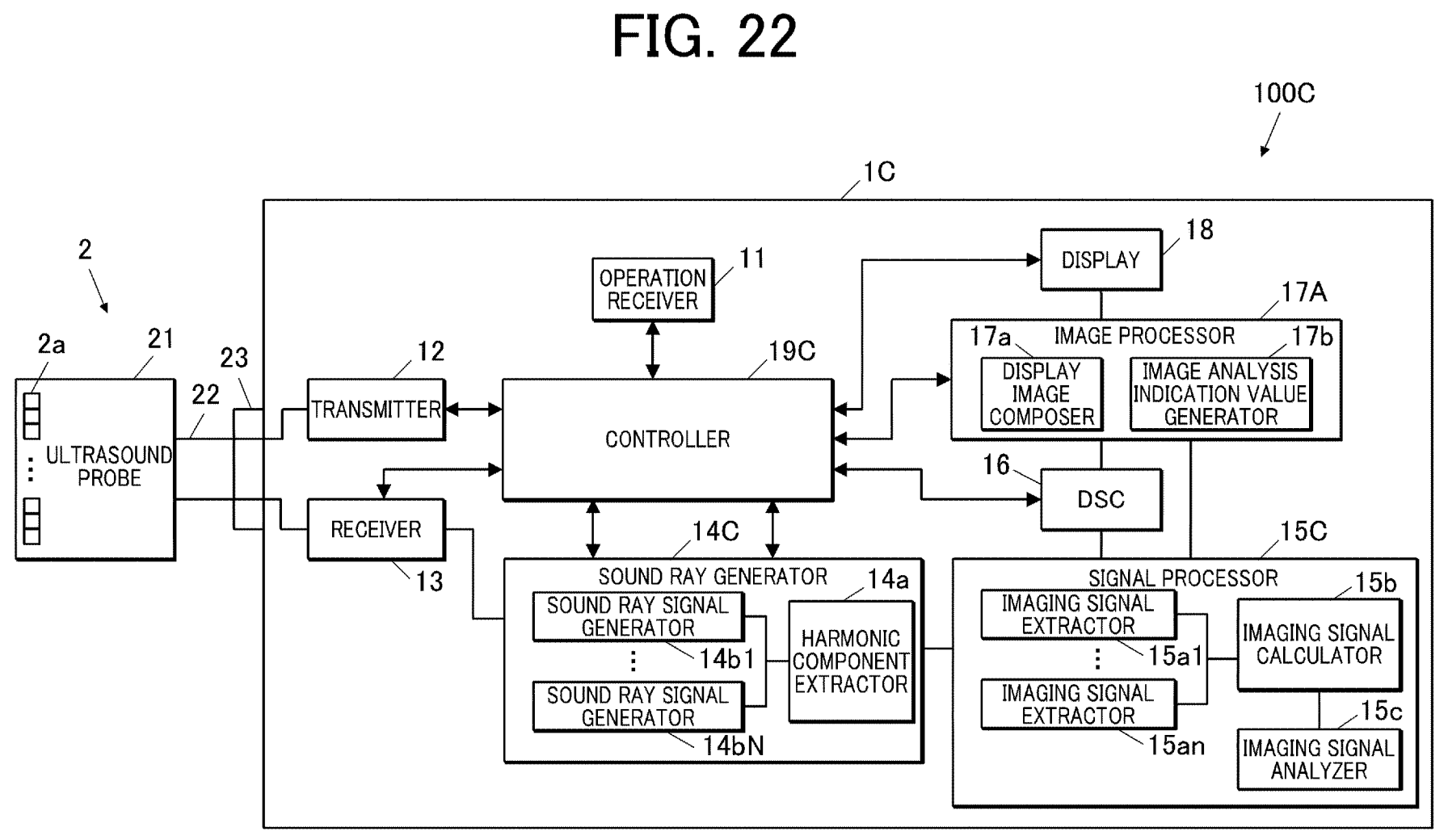

FIG. 22 is a block diagram showing functional components of the diagnostic ultrasound apparatus in a third embodiment;

FIG. 23 is a flowchart of a third ultrasound-image display process;

Figure 24:
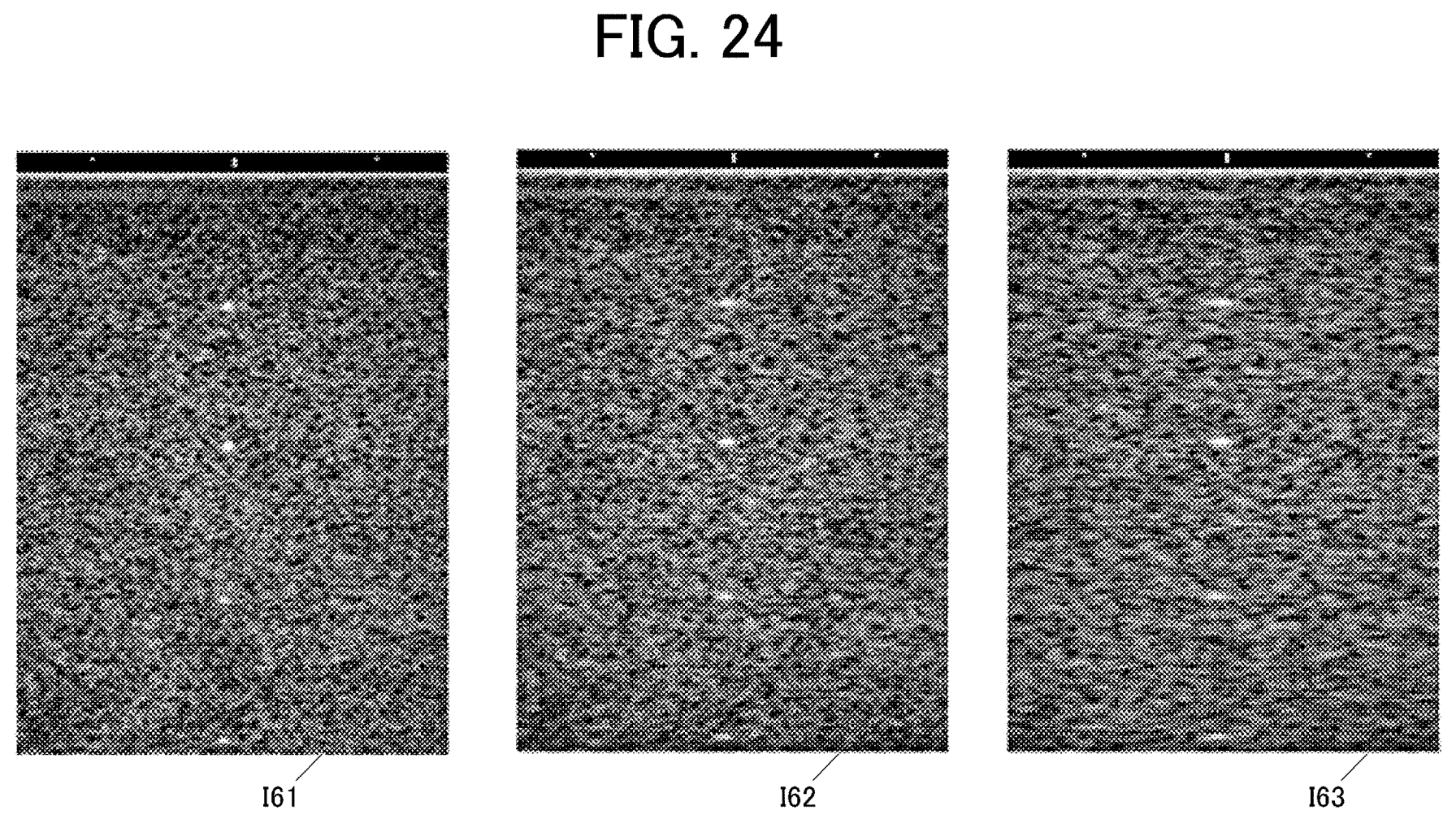

FIG. 24 shows ultrasound images subjected to different phase-and-sum conditions;

FIG. 25 shows watershed division images corresponding to the ultrasound images shown in FIG. 24; and FIG. 26 is a flowchart of a fourth ultrasound-image display process.

DETAILED DESCRIPTION OF THE EMBODIMENTS

Hereinafter, embodiments of the present invention are described with reference to the drawings. However, the scope of the present invention is not limited to the disclosed embodiments.

First Embodiment

Figure 1:
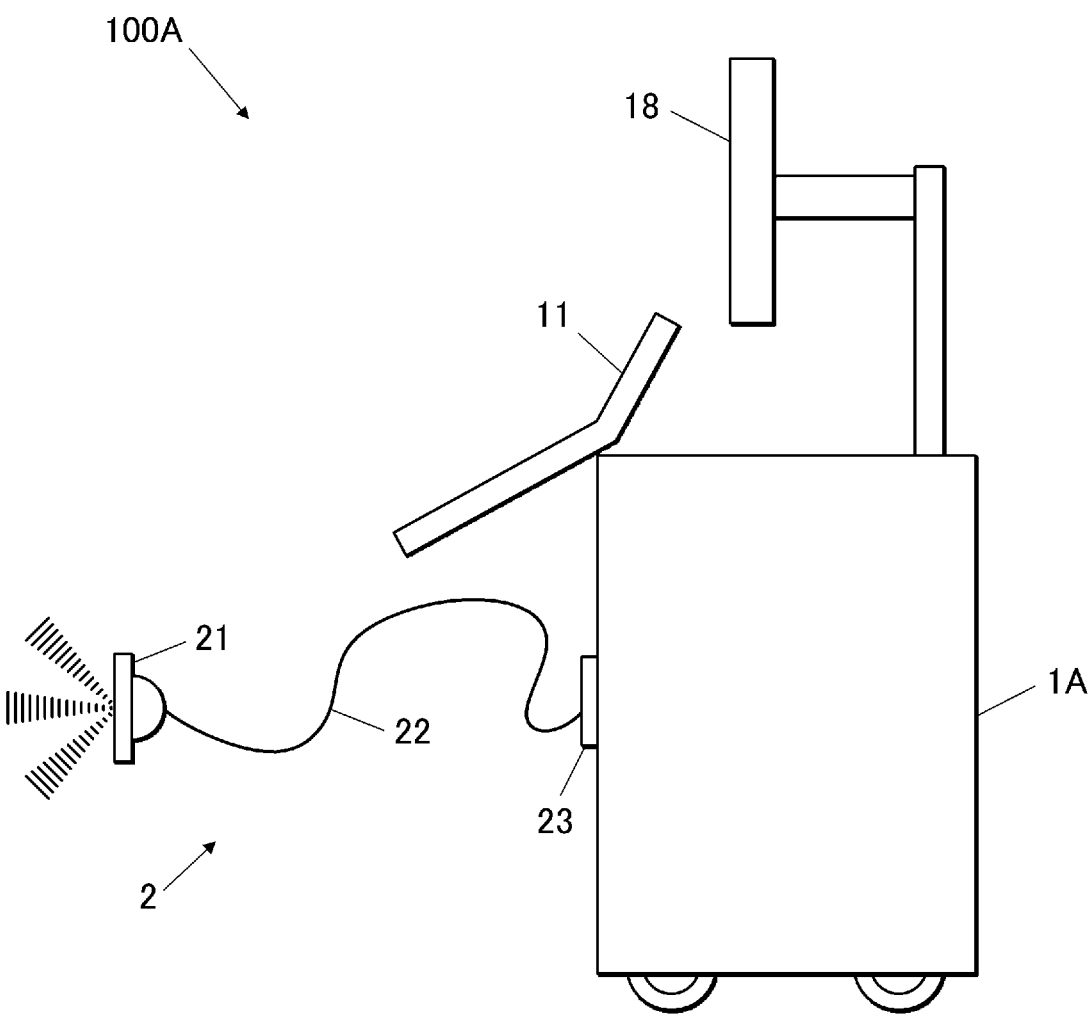
FIG. 1 is an external view of a diagnostic ultrasound apparatus in a first embodiment of the present invention.
Figure 3:
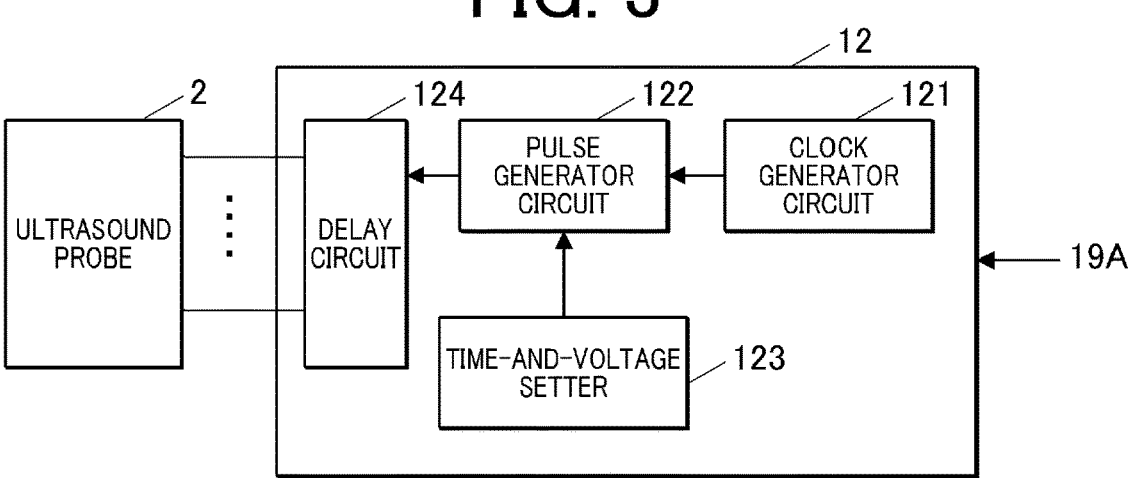
FIG. 3 is a block diagram showing functional components of a transmitter.
Figure 4A:
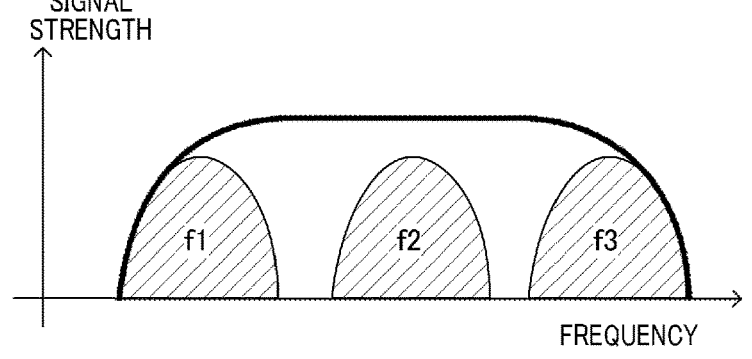
FIG. 4A shows frequency characteristics of the signal strength of transmitted ultrasound.
Figure 4B:
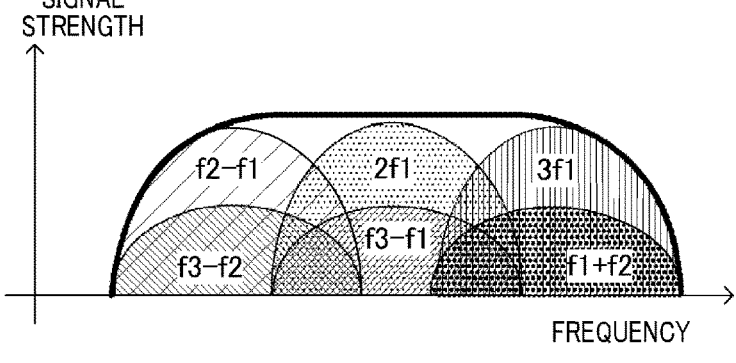
FIG. 4B shows frequency characteristics of the signal strength of reflected ultrasound.
Figure 5:
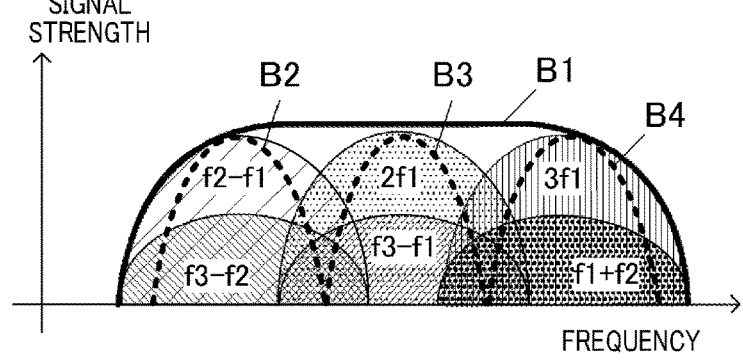
FIG. 5 shows frequency characteristics of the signal strength of first to fourth bands in the reflected ultrasound.

The first embodiment of the present invention is described with reference to FIG. 1 to FIG. 19. Firstly, the configuration of a diagnostic ultrasound apparatus 100A in this embodiment is described with reference to FIG. 1 to FIG. 8. FIG. 1 is an external view of the diagnostic ultrasound apparatus 100A in the first embodiment. FIG. 2 is a block diagram showing a schematic configuration of the diagnostic ultrasound apparatus 100A. FIG. 3 is a block diagram showing functional components of a transmitter 12. FIG. 4A shows frequency characteristics of the signal strength of transmitted ultrasound. FIG. 4B shows frequency characteristics of the signal strength of reflected ultrasound. FIG. 5 shows frequency characteristics of the signal strength of first band B1 to fourth band B4 in the reflected ultrasound.

The diagnostic ultrasound apparatus 100A in this embodiment is installed in medical facilities, such as hospitals, and includes an diagnostic ultrasound apparatus main body 1A and an ultrasound probe 2, as shown in FIG. 1 and FIG. 2. The ultrasound probe 2 transmits ultrasound (transmitted ultrasound waves) to a not-illustrated subject, such as a living body, and receives reflected ultrasound (reflected ultrasound waves: echoes) reflected in the subject. The ultrasound probe 2 includes an ultrasound probe main body 21, a cable 22, and a connector 23. The ultrasound probe main body 21 is a header of the ultrasound probe 2 that transmits and receives ultrasound. The cable 22 connects the ultrasound probe main body 21 and the connector 23. Through the cable 22, drive signals for the ultrasound probe main body 21 and reception signals (ultrasound waves) flow. The connector 23 is a plug connector to be connected to a not-illustrated receptacle connector of the diagnostic ultrasound apparatus main body 1A.

The ultrasound diagnostic apparatus main body 1A is connected to the ultrasound probe main body 21 via the connector 23 and the cable 22. The ultrasound diagnostic apparatus main body 1 sends drive signals, which are electronic signals, to the ultrasound probe main body 21 to cause the ultrasound probe main body 21 to transmit transmission ultrasound toward the subject. When the ultrasound probe main body 21 receives reflected ultrasound waves from inside the subject, the ultrasound probe 2 generates reception signals, which are electric signals. On the basis of the generated reception signals, the ultrasound diagnostic apparatus main body 1 images the internal state of the subject by generating ultrasound image data. The ultrasound diagnostic apparatus main body 1 may wirelessly communicate with the ultrasound probe 2 (ultrasound probe main body 21) over an ultra wide band (UWB), instead of communicating via the cable 22.

As shown in FIG. 2, the ultrasound probe main body 21 is equipped with a plurality of transducers 2a made of piezoelectric elements. The transducers 2 are arranged in one-dimensional array in the azimuthal direction, for example. In this embodiment, the ultrasound probe 2 includes 192 transducers 2a, for example. The transducers 2a may be arranged in two-dimensional arrays. The number of transducers 2a may be determined as desired. This embodiment uses a linear-scanning electronic scan probe as the ultrasound probe 2. However, the ultrasound probe may be an electronic scan type or a mechanical scanning type. Further, the ultrasound probe may be a linear scanning type, sector scanning type, or convex scanning type.

It is preferable that the frequency characteristic of the ultrasound probe 2 used in the present invention be a wide bandwidth, although the frequency value thereof is not limited. With a narrow band, the correlation difference between high-correlation imaging signals by the reflection tissues and low-correlation imaging signals by scatter tissues and interference becomes small. When an arithmetic operation is performed among bandwidth-divided image signals, low-correlation imaging signals may not be sufficiently suppressed. Specifically, it is preferable that the fractional bandwidth be at least equal to or greater than 100%, or more preferably, equal to or greater than 120% for the fractional bandwidth of −20 dB, which is a realistic effective band for transmission and reception.

The diagnostic ultrasound apparatus main body 1A includes, for example, an operation receiver 11, a transmitter 12, a receiver 13, a sound-ray signal generator 14A, a signal processor 15A, a digital scan converter (DSC) 16 as an image data generator, an image processor 17A as a first/ second display controller, a display 18, and a controller 19A, as shown in FIG. 2.

The operation receiver 11 includes operation tools for a user (e.g., doctor, sonographer) to input commands to start diagnosis or to input data (e.g., personal information of a subject). For example, the operation receiver 11 includes various switches, buttons, trackballs, a mouse, a keyboard, a touchscreen, and/or a multi-functional switch. The operation receiver 11 receives operation inputs by the user via the operation tools and output operation signals corresponding to the input to the controller 19A.

The transmitter 12 is a circuit that supplies drive signals (electric signals) to the ultrasound probe main body 21 via the cable 22 and the connector 23 under the control of the controller 19A so that the ultrasound probe 2 generates transmission ultrasound. As shown in FIG. 3, the transmitter 12 includes a clock generator circuit 121, a pulse generator circuit 122, a time-and-voltage setter 123, and a delay circuit 124, for example.

The clock generator circuit 121 generates clock signals that determine timings to transmit drive signals and transmission frequency. The pulse generator circuit 122 generates pulse signals (drive signals) at a predetermined cycle. For example, the pulse generator circuit 122 can generate square-wave drive signals by switching output voltages among three values (+HV, 0 (GRD), −HV) or among five values (+HV, +MV, 0 (GRD), −MV, −HV). In the above, the amplitude of the pulse signals is the same in the positive and negative polarities. The amplitude is not limited to this, though. Although the drive signals are output by switching voltages among three or five values in this embodiment, the number of voltage values is not limited to three or five but may be set to a desired value. However, it is preferable that the value be equal to or less than five in order to improve flexibility for controlling frequency components at low cost and to improve resolution of transmission ultrasound.

The time-and-voltage setter 123 sets the duration of each period during which the drive signal output from the pulse generator circuit 122 is at the same voltage level and the voltage level of the drive signal. Specifically, the pulse generator circuit 122 outputs the pulse-wave drive signals in which the duration of each period and voltage levels are set by the time-and-voltage setter 123. The duration of each period and the voltage level set by the time-and-voltage setter 123 may be adjustable by input operations through the operation receiver 11, for example.

The delay circuit 124 sets a delay time for transmitting drive signals to respective individual pathways corresponding to respective transducers 2a and delays transmission of drive signals by the set delay time. The delay circuit thus converges transmission beams, which consist of transmission ultrasound.

Under the control of the controller 19A, the transmitter 12 as configured above successively shifts the transducers 21a to which the drive signals are supplied by a predetermined number of transducers each time ultrasound is transmitted/ received, thereby supplying the drive signals to the respective selected transducers 2a. Thus, scanning is performed.

In this embodiment, pulse inversion can be performed to extract harmonic components, which are described later. That is, when pulse inversion is performed, the transmitter 12 can transmit a first pulse signal and a second pulse signal that is polarity-reversed from the first pulse signal onto the same scanning line at time intervals. The second pulse signal may be a signal that is polarity-reversed from the first pulse signal after at least one of multiple duties of the first pulse signal is changed. The second pulse signal may also be a signal that is time-reversed from the first pulse signal.

The receiver 13 is a circuit that receives reception signals (electric signals) from the ultrasound probe 2 (ultrasound probe main body 21) via the cable 22 and the connector 23 under the control of the controller 19A.

The sound-ray signal generator 14A is a circuit that generates sound ray signals on the basis of the reception signals received by the receiver 13 under the control of the controller 19A. The sound-ray signal generator 14A includes a harmonic component extractor 14*a*, an amplifier, an A/D converter circuit, and a phase-and-sum circuit, for example.

The amplifier is a circuit that amplifies reception signals received by the receiver 13 at a predetermined amplification factor for each of the individual pathways corresponding to each of the transducers 2*a*. The A/D converter circuit converts the amplified reception signals by A/D conversion. The phase-and-sum circuit aligns the time phases of the A/D converted reception signals by adding delay times for the respective individual pathways corresponding to the respective transducers 2*a* and sums (phases and sums) the aligned reception signals to generate digital sound ray signals (sound ray data).

The harmonic component extractor 14*a* extracts harmonic components from the generated sound ray signals by pulse inversion under the control of the controller 19A. In this embodiment, the harmonic component extractor 14*a* can extract a signal component(s) mainly composed of the second harmonic. The second harmonic component can be extracted by summing (combining) reception signals obtained from reflected ultrasound waves corresponding to two transmission ultrasound waves generated from two pulse signals (the above-described first and second pulse signals); removing fundamental components in the reception signals; and performing filtering. When an odd-order harmonic component, such as the third harmonic, is used, the harmonic component can be extracted by subtracting first and second reception signals corresponding to the respective first and second pulse signals and then removing the fundamental components with a filter or the like. Both the even-order harmonic component obtained by addition and the odd-order harmonic component obtained by subtraction may be used. In this case, phase adjustment is performed as needed with an all-pass filter or the like such that the phase of an odd-order harmonic reception signal(s) matches the phase of an even-order harmonic reception signal(s), and they are added up (combined) at the stage of reception signals before envelope demodulation. Accordingly, the frequency band of the even-order harmonic reception signal and the frequency band of the odd-order harmonic reception signal are combined, and a reception signal(s) having a wider band can be obtained.

For example, the transmitter 12 generates a drive signal for transmitting transmission ultrasound that includes fundamentals f1, f2, f3 as shown in FIG. 4A. In FIG. 4A, the horizontal axis represents frequency; the vertical axis represents signal strength (sensitivity) of transmission ultrasound; and the solid line represents the frequency band of the ultrasound probe 2. The same applies to FIG. 4B, which shows the signal strength of reflected ultrasound.

FIG. 4B shows harmonic components of reflected ultrasound that are obtained as frequency components of the reception signal by the receiver 13 and the sound-ray signal generator 14A and that correspond to the transmission ultrasound having the fundamentals f1, f2, f3. Specifically, frequency components that have the frequencies of f3–f2, f2–f1, f3–f1, 2f1, f1+f2, 3f1, respectively are obtained as the harmonic components of the reflected ultrasound. The frequencies of f3–f2, f2–f1, f3–f1, 2f1, f1+f2, 3f1 are derived at least one of the fundamentals f1, f2, f3. The sound-ray signal generator 14A generates sound ray signals including all the frequency components shown in FIG. 4B.

The signal processor 15A includes: imaging signal extractors 15*a*1 to 15*an* (n: a natural number equal to or greater than 2) that serve as an imaging signal generator; an imaging signal calculator 15*b* that serves as a calculator; and an imaging signal analyzer 15*c* that serves as an analyzer. Under the control of the controller 19A, the signal processor 15A extracts signals corresponding to the respective n frequency bands from the sound ray signal input by the harmonic component extractor 14*a* and generates the first to the n-th imaging signals; the signal processor 15A performs an arithmetic operation among the first to n-th imaging signals to generate an arithmetically-processed imaging signal; and the signal processor 15A performs analysis processing on the basis of the normal image signal corresponding to a normal image(s) on which the arithmetic operation is not performed (the normal image before the arithmetic operation is performed) and the arithmetically-processed imaging signal.

The imaging signal extractors 15*a*1 to 15*an* are circuits that include first to n-th band pass filters, respectively for passing reception signals of the first to n-th frequency bands. Under the control of the controller 19A, the imaging signal extractors 15*a*1 to 15*an* pass the frequency components in the sound ray signals input by the harmonic component extractor 14*a* through their respective band pass filters, thereby extracting first to n-th imaging signals. For example, the imaging signal extractor 15*a*1 passes the frequency component of the frequency band of the ultrasound probe 2 (full band) through the first band pass filter, thereby outputting a first imaging signal. The imaging signal extractors 15*a*2 to 15*an* pass the frequency components of the frequency bands that are narrower than the full band through the second to n-th band pass filters, respectively, thereby outputting the second to n-th imaging signals. The first imaging signal contains the largest amount of high-frequency components.

The cutoff characteristics of the different band pass filters for the respective imaging signal extractors 15*a*1 to 15*an* are determined appropriately depending on the acoustic characteristic and the observation target of the ultrasound probe 2. There may be multiple combinations of cutoff characteristics prepared. Selection of a combination among the combinations may be done automatically or manually. For example, a combination may be selected automatically according to the observation target (part of the subject) selected by the user through the operation receiver 11. A combination may also be selected automatically so as to adapt with the evaluation value of the feature quantities extracted from the imaging signals. A combination may also be selected by the user as needed via the operation receiver 11. These band pass filters may not be fixed filters but may be so-called dynamic filters the cutoff characteristics of which change successively depending on the depth.

For example, consider the case of n=4. The imaging signal extractor 15$a$1 performs filtering on the sound ray signal, which is generated by the sound-ray signal generator 14A, using the first band pass filter to generate the first imaging signal. The first band pass filter corresponds to the full band B1 shown by the solid line in FIG. 5 and passes all the frequency components shown in FIG. 5. Herein, the imaging signal extracted by the imaging signal extractor 15$a$1 and corresponding to the full band B1 is a normal imaging signal. The normal imaging signal corresponds to the normal image. However, the normal imaging signal may be a sound ray signal generated by the sound-ray signal generator 14A and not filtered by the imaging signal extractors 15$a$1 to 15$an$.

The imaging signal extractor 15$a$2 performs filtering on the sound ray signal, which is generated by the sound-ray signal generator 14A, using the second band pass filter to generate the second imaging signal. The second band pass filter corresponds to the low-frequency band B2 shown by the dotted line in FIG. 5. The imaging signal extractor 15$a$3 performs filtering on the sound ray signal, which is generated by the sound-ray signal generator 14A, with the third band pass filter to generate the third imaging signal. The third band pass filter corresponds to the band B3 shown by the dotted line in FIG. 5 and corresponding to higher frequencies than the band B2. The imaging signal extractor 15$a$4 performs filtering on the sound ray signal, which is generated by the sound-ray signal generator 14A, using the fourth band pass filter to generate the fourth imaging signal. The fourth band pass filter corresponds to the band B4 shown by the dotted line and corresponding to higher frequencies than than the band B3.

The imaging signal calculator 15$b$ performs an arithmetic operation among the first to n-th imaging signals, which are generated by the imaging signal extractors 15$a$1 to 15$an$ for generating B-mode (brightness mode) image data, to generate an arithmetically-processed imaging signal under the control of the controller 19A. The arithmetic operation is a calculation to suppress scatter components that correspond to ultrasound scattered by scatter sources (small scatters) in the subject while retaining reflection components that correspond to ultrasound reflected by tissues (reflectors) in the subject. The arithmetic operation utilizes correlation differences for different frequencies. When the brightness correlation at the same point (the same position) among multiple ultrasound images is high, high-brightness reflection components appear, whereas when the brightness correlation at the same position among multiple ultrasound images is low, low-brightness scatter components appear. The arithmetic operation utilizes this phenomenon. As described below, it is preferable that multiplication, which requires light processing load, be performed as the arithmetic operation in order to suppress scatter components. Multiplication of the first to n-th imaging signals is the multiplication of brightness values of pixels at the same position in the respective B-mode images that correspond to the respective first to n-th imaging signals. When any one of brightness values of pixels at the same position in the first to n-th imaging signals is zero (i.e., black), the multiplication result is zero.

The imaging signal calculator 15$b$ further performs a gradation adjustment process on the generated arithmetically-processed imaging signal under the control of the controller 19A. The gradation adjustment process is, for example, the power root calculation process and/or the lookup table (LUT) conversion process. When the imaging signal calculator 15$b$ performs multiplication as the arithmetic operation and the multiplication product values are directly converted into brightness values, only the bright parts are emphasized and the tissues/organizations are less visible in the resulted image. It is therefore preferable that the gradation adjustment process be performed. Specifically, the power root calculation process is performed on the basis of the number of images used in the arithmetic operation. For example, when the number of multiplied images is three, the cube root of the multiplication product is calculated. Similarly, when n=4 as shown in FIG. 5 and the number of multiplied images is four, the fourth root of the multiplication product is calculated. Thus, the gradation can be adjusted relatively easily. Instead of the individual calculation, a corresponding LUT may be used, and the gradation may be adjusted by the LUT conversion process. The LUT is created and stored beforehand in a not-illustrated storage, such as the read only memory (ROM) of the controller 19A or the hard disk drive (HDD)/solid state drive (SDD) of the diagnostic ultrasound apparatus 100A, for example.

The imaging signal analyzer 15$c$ analyzes the arithmetically-processed imaging signal, which is calculated by the imaging signal calculator 15$b$, under the control of the controller 19A. The analysis includes a process of generating a difference imaging signal of a difference image. The difference imaging signal is obtained by calculating the difference between the normal imaging signal and the arithmetically-processed imaging signal. The difference is calculated by subtracting, from each brightness value of each pixel at a position in the normal image (normal imaging signal), a brightness value of the corresponding pixel at the same position in the arithmetically-processed image (arithmetically-processed imaging signal). The difference image shows extracted scatter components. The above analysis further includes a process of generating an index value(s) based on the difference image of the generated difference imaging signal. The index value based on the difference image is information for diagnosing a patient (subject), for example. As a specific example, the index value based on the difference image may be statistical information, such as the average of difference values or the variance of difference values in a region of interest (ROI). The ROI may be set by the user via the operation receiver 11, for example. Multiple ROIs may be set, and the index value may be a statistical value among the multiple ROIS (e.g., average of difference values, variance of difference values). When the index value is displayed, the user can recognize the amount of scatter components or the ratio of scatter components in the ROI. Further, the index value can be utilized as information indicating the intramuscular fat quantity in each part of skeletal muscle, for example. By observing the index value at a specific part over time, the user may be able to utilize the index value for judging effectiveness of rehabilitation.

The method for transmitting and receiving ultrasound for generating a B-mode image, to which the present invention is applied, is not limited to the above-described harmonic imaging mode. However, it is preferable that a method allow transmission and reception of ultrasound with high contrast and wide frequency band. Specifically, it is preferable that harmonic imaging be used that depends on the sound pressure in generating harmonic components and therefore generates less artifacts (e.g., sidelobe) and that yields high-contrast image signals. In particular, Japanese patent No. 6326716, No. 6443217, or No. 6540838 may be preferably used because they yield wide-range reception signals from both shallow and deep parts. By obtaining wide-band reception signals from both the shallow and deep parts and performing the arithmetic operation among multiple images obtained by bandwidth division, low-correlation signals can be suppressed effectively.

Under the control of the controller 19A, the DSC 16 performs envelope demodulation and logarithmic compression on the normal imaging signal (sound ray signal) input from the imaging signal extractor 15a1, the arithmetically-processed imaging signal (sound ray signal) input by the imaging signal calculator 15b, and the difference imaging signal (sound ray signal) input from the imaging signal analyzer 15c; the DSC 16 further adjusts the dynamic range and the gain to convert the signals into brightness; the DSC 16 further performs polar coordinate conversion and calculation for interpolation of display pixels as desired; and the DSC16 thus generates normal image data, arithmetically-processed image data, and difference image data as B-mode image data for display. The B-mode image data shows the intensity of reception signals by brightness.

The image processor 17A is a circuit that performs image processing on the normal image data, arithmetically-processed image data, and difference image data input by the DSC 16 and on the index value based on the difference image input by the imaging signal analyzer 15c via the DSC 16 under the control of the controller 19A. The image processor 17A includes a display image composer 17a and an image analysis indication value generator 17b.

Under the control of the controller 19A, the display image composer 17a generates combined image data for display by combining at least two among the normal image data input by the DSC 16, the arithmetically-processed image data input by the DSC 16, the difference image data for display input by the image analysis indication value generator 17b, and the index value based on the difference image. In the combined image data, the at least two display contents are arranged side by side.

The image analysis indication value generator 17b is a circuit that generates the difference image data for display on the basis of difference image data input by the DSC 16 under the control of the controller 19A. For example, the image analysis indication value generator 17b colors the pixels constituting the difference image data on the basis of the difference values, and generates the colored difference image data as the difference image data for parametric display. The image analysis indication value generator 17b also generates the index value based on the difference image for display, on the basis of the index value based on the difference image input by the imaging signal analyzer 15c via the DSC 16.

The display 18 may be a liquid crystal display (LCD), a cathode ray tube (CRT) display, an organic electronic luminescent display (ELD), a nonorganic EL display, or a plasma display, for example.

Under the control of the controller 19A, the display 18 displays an ultrasound image and so forth on the display screen in accordance with display signals of image data and combined image data input by the image processor 17A.

The controller 19A includes a central processing unit (CPU), a read only memory (ROM), and a random access memory (RAM), for example. The controller 19A reads various processing programs, such as a system program stored in the ROM, loads the programs into the RAM, and centrally controls the operation of each component of the diagnostic ultrasound apparatus 100A in accordance with the loaded programs. The ROM consists of a non-volatile memory, such as a semiconductor, for example. The ROM stores the system program for the diagnostic ultrasound apparatus 100A, various processing programs executable on the system program, and various kinds of data. These programs are stored in the form of computer-readable program codes, and the CPU sequentially executes operations in accordance with the program codes. The ROM stores a first ultrasound image display program for executing a first ultrasound image display process, which is described later. The RAM provides a working area for temporarily storing various programs to be executed by the CPU and data relating to the programs.

Regarding the components of the diagnostic ultrasound apparatus main body 1A, the functions of part or all of the functional blocks thereof can be achieved by a hardware circuit, such as an integrated circuit. The integrated circuit is a large scale integration (LSI), for example. Depending on the degree of integration, an LSI may also be called an IC (integrated circuit), a system LSI, a super LSI, or an ultra LSI. The integrated circuit may be achieved not by an LSI but by a dedicated circuit or a general-purpose processor. A field programmable gate array (FPGA) or a reconfigurable processor that is reconfigurable in terms of connections and settings of circuit cells in an LSI may also be used. Alternatively, the functions of part or all of the functional blocks can be achieved by a software. In this case, the software is stored in at least one storage medium such as a ROM, an optical disk, or a hard disk, and the software is executed by an arithmetic processor.

Figure 6:
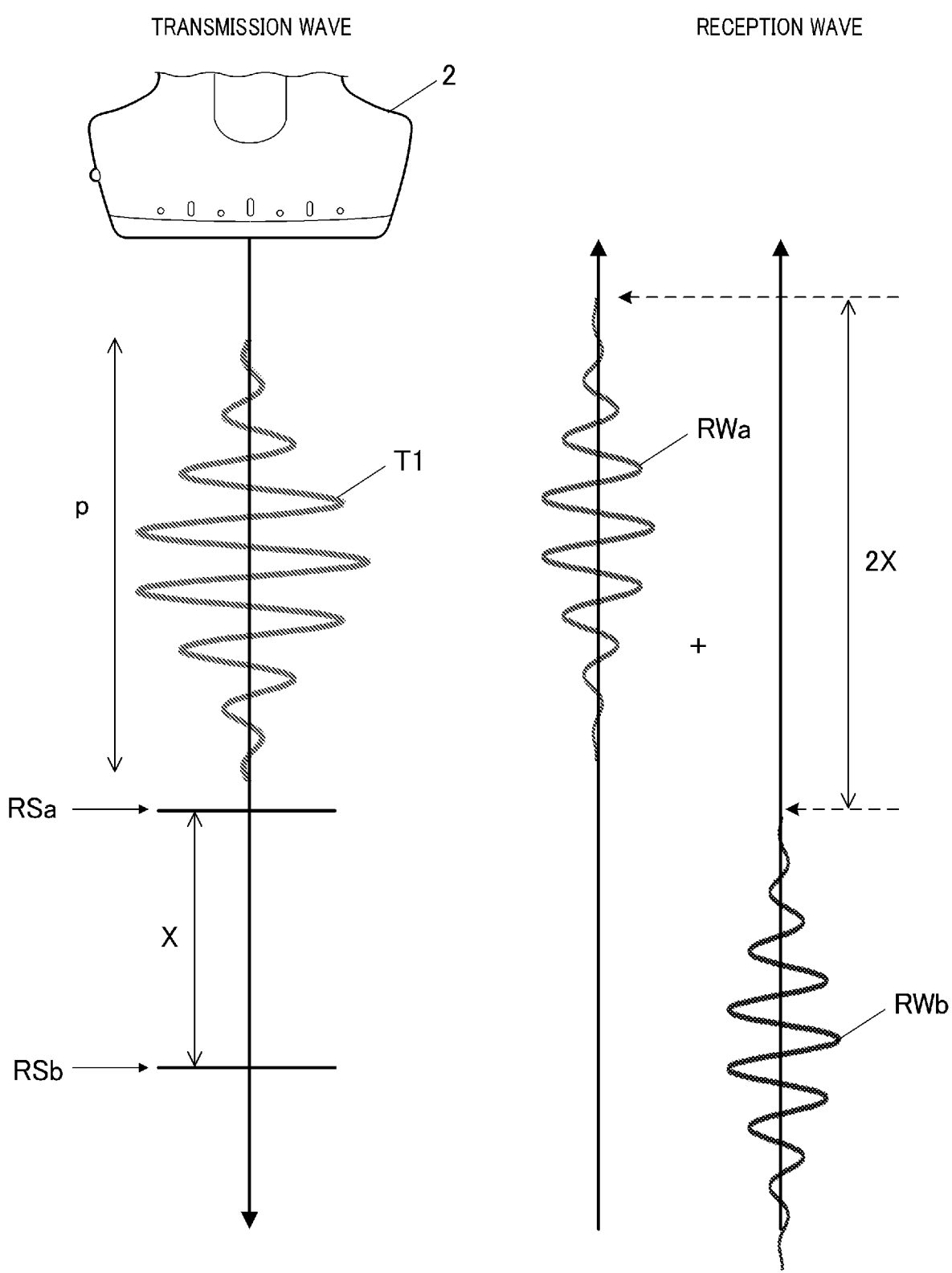
FIG. 6 shows a transmission wave from an ultrasound probe and reflected waves from reflection surfaces.
Figure 7:
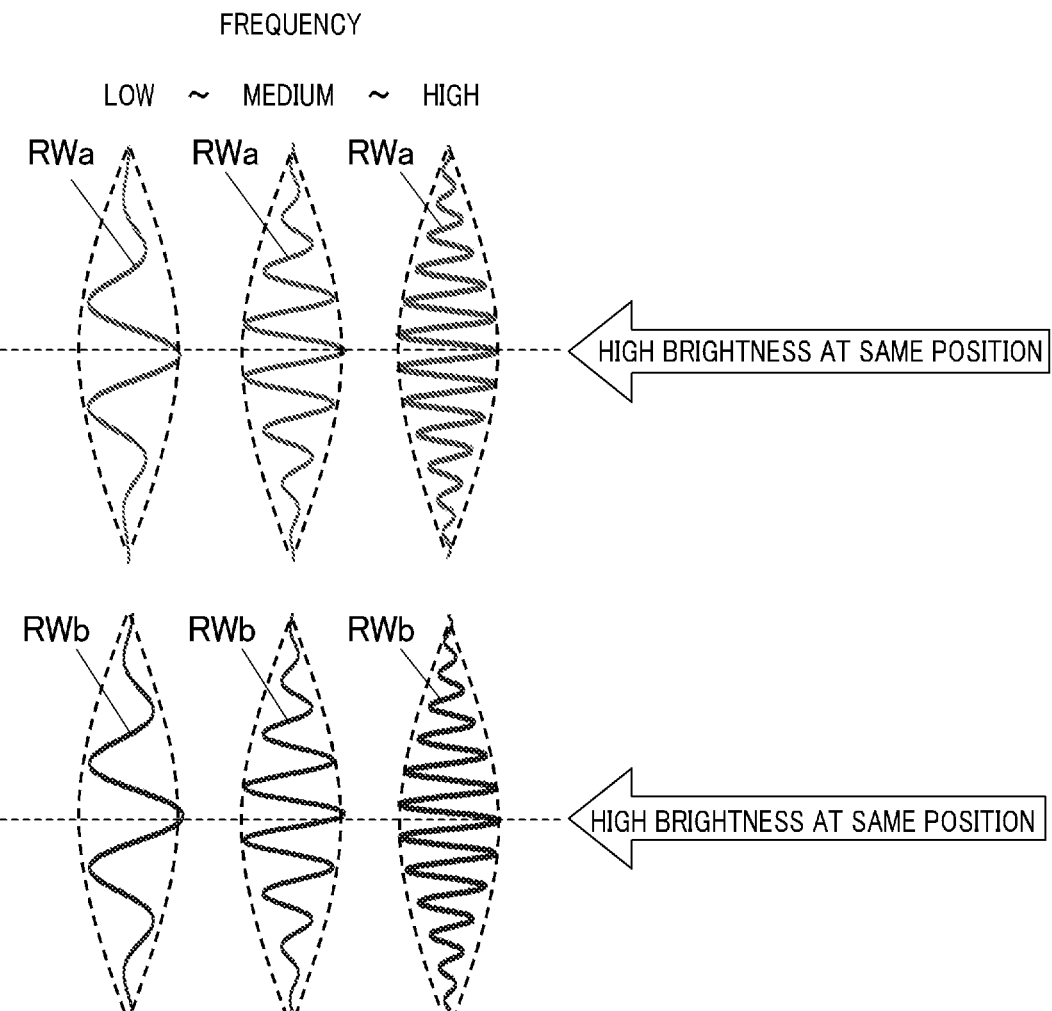
FIG. 7 shows high brightness positions of reflected waves when an imaging frequency is changed.
Figure 8:
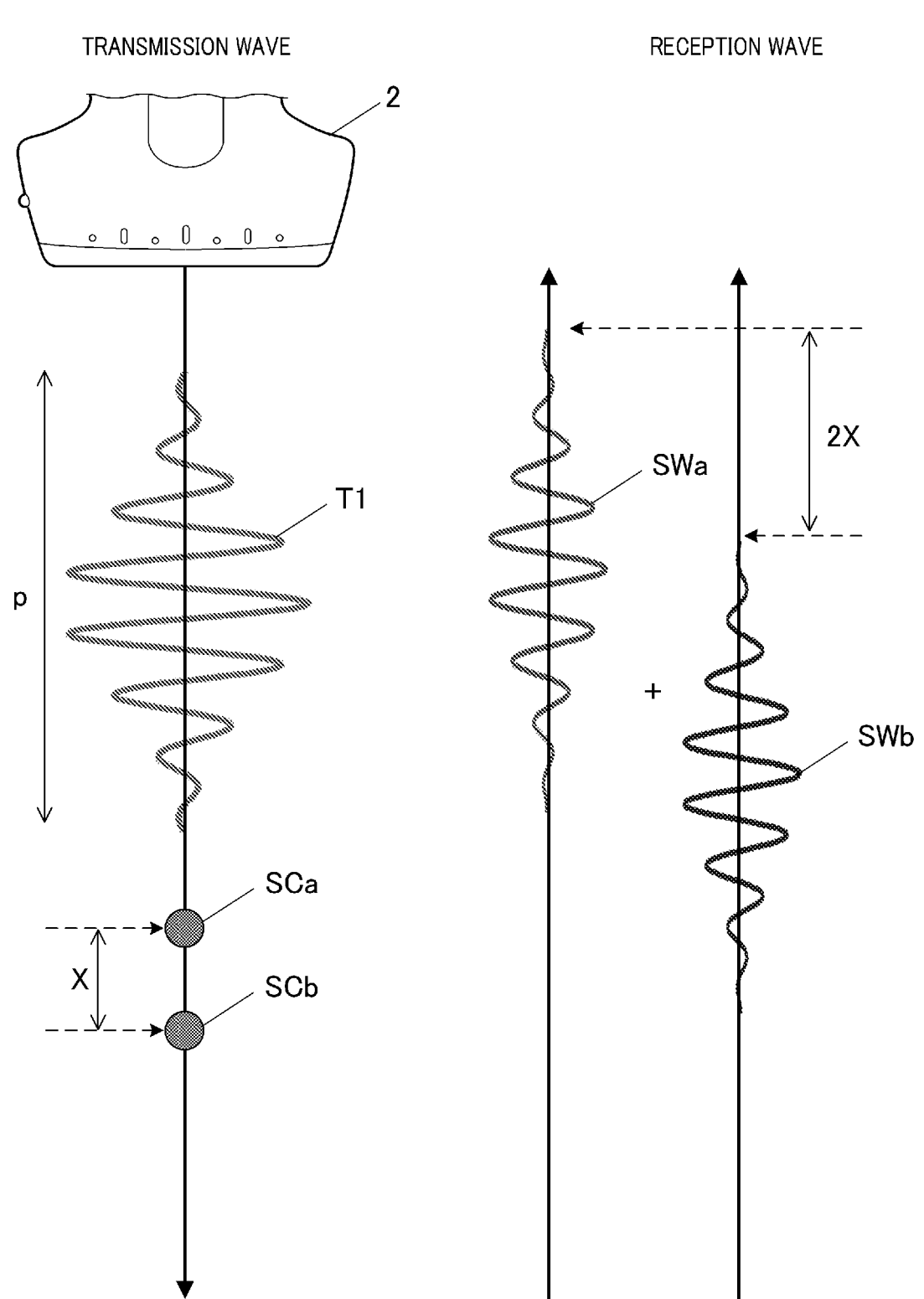
FIG. 8 shows a transmission wave from the ultrasound probe and scattered waves from scatter sources.

Herein, differences in correlation between reflected signals and scattered signals of an ultrasound image are described with reference to FIG. 6 to FIG. 11. FIG. 6 shows a transmission wave T1 transmitted from the ultrasound probe 2 and reflected waves RWa, RWb reflected by the reflection surfaces RSa, RSb. FIG. 7 shows high brightness positions of the reflected waves RWa, RWb with respect to different imaging frequencies. FIG. 8 shows a transmission wave T1 transmitted from the ultrasound probe 2 and scattered waves SWa, SWb scattered by scatter sources SCa, SCb.

Figure 9A:
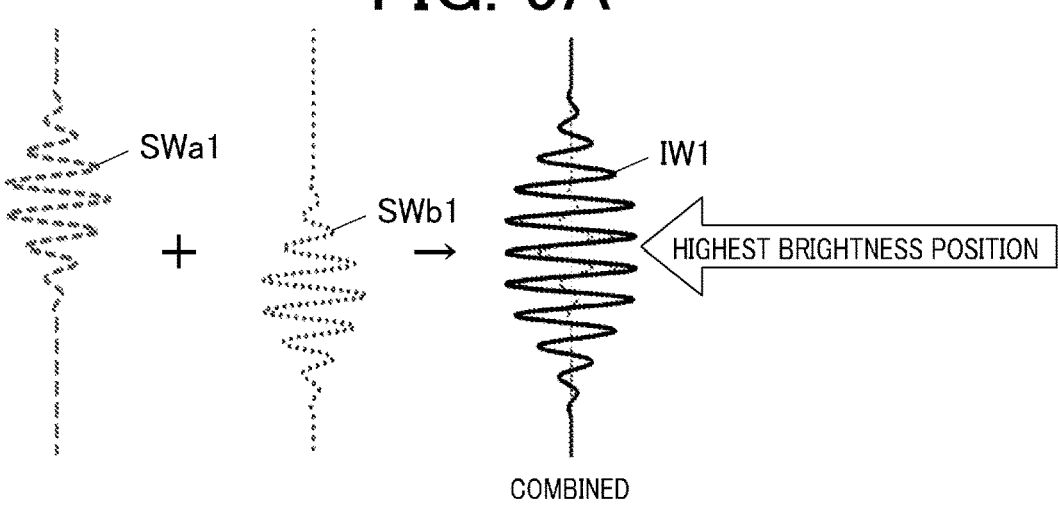
FIG. 9A shows a scattered wave and an interference wave having the same phase.

FIG. 9A shows the scattered waves SWa1, SWb1 in the same phase and an interference wave IW1.

Figure 9B:
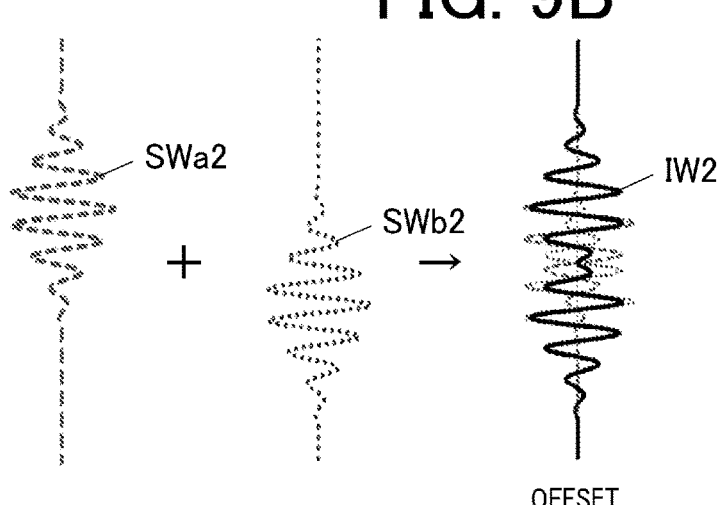
FIG. 9B shows a scattered wave and an interference wave having opposite phases.
Figure 9C:
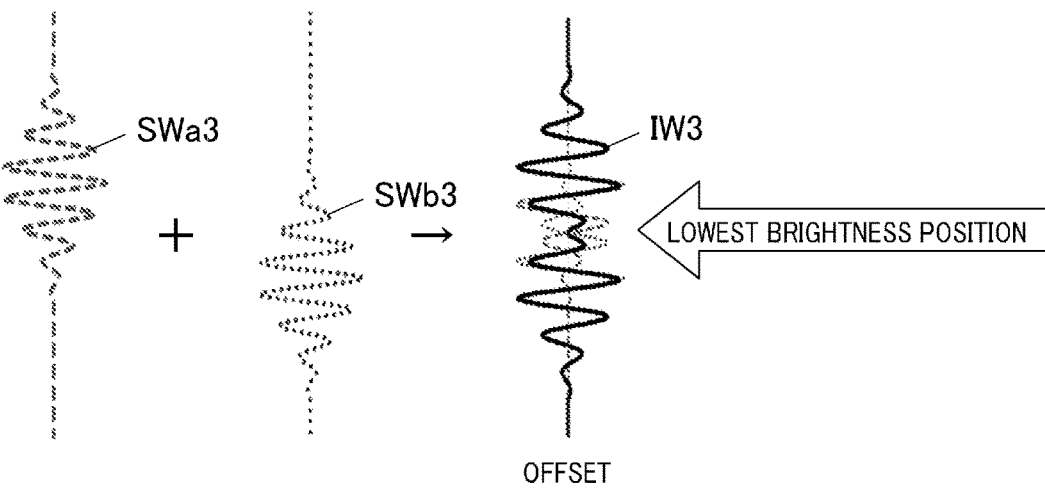
FIG. 9C shows a scattered wave and an interference wave when the imaging frequency is lowered than in FIG. 9A.

FIG. 9B shows the scattered waves SWa2, SWb2 in opposite phases and an interference wave IW2. FIG. 9C shows scattered waves SWa3, SWb3 with a lower imaging frequency than in FIG. 9A and an interference wave IW3.

FIG. 10A shows an example of an ultrasound image with less scattering virtual images. FIG. 10B shows an example of an ultrasound image with more scattering virtual images. FIG. 11 shows the ultrasound probe 2, the scatter sources SC1, SC2, SC3, and virtual images V1, V2, V3 of the scatter sources SC1, SC2, SC3.

As shown in FIG. 6, consider a case where the transmission wave T1 (transmitted ultrasound) is transmitted toward the subject by the ultrasound probe 2, reflected on the reflection surfaces RSa, RSb of reflectors (e.g., tissues of the subject in different depths), and received as reception waves by the ultrasound probe 2. The ultrasound reflected by the reflection surface RSa is the reflected wave RWa (reception wave), and the ultrasound reflected by the reflection surface RSb is the reflected wave RWb (reception wave). The width of the transmission wave T1 in the transmitted direction is the pulse width p. The distance between the reflection surface RSa and the reflection surface RSb in the depth direction is the distance X.

The distance between the reflected wave RWa and RWb is the distance 2X. When "2X>p" holds, the reflected waves RWa, RWb are received by the ultrasound probe 2 without interfering with each other, the received reflected waves RWa, RWb are imaged as brightness points corresponding to their respective pulse widths and amplitudes.

As shown in FIG. 7, assume that the imaging frequency of the reflected waves RWa, RWb is changed in three levels: low, medium, and high. When the distance between the reflection surfaces RSa, RSb is sufficiently greater than the wavelength (pulse width p), the reflectances of the respective reflection surfaces RSa, RSb are determined by the acoustic impedances and remain constant with different imaging frequencies. Further, the pulses (reflected waves RWa, RWb) do not interfere with each other or offset each other. Accordingly, the reflected waves RWa with respect to different imaging frequencies (low, medium, high) have the high brightness at the same position. Similarly, the reflected waves RWb with respect to different imaging frequencies (low, medium, high) have the high brightness at the same position. Thus, the brightness correlation at the same position is high.

Next, as shown in FIG. 8, consider a case where the transmission wave T1 (transmitted ultrasound) is transmitted toward the subject by the ultrasound probe 2, scattered by scatter sources SCa, SCb, and received as reception waves by the ultrasound probe 2. The scatter sources SCa, SCb are dense scatter sources in different depths of the subject. The ultrasound (echo) scattered by the scatter source SCa is the scattered wave SWa as the reception wave, and the ultrasound scattered by the scatter source SCb is the scattered wave SWb as the reception wave. The width of the transmission wave T1 in the transmission direction is the pulse width p. The distance between the scatter source SCa and the scatter source SCb in the depth direction is the distance X.

The distance between the scattered wave SWa and the scattered wave SWb is the distance 2X. When "2X<p" holds, the scattered waves SWa, SWb interfere with each other and are received by the ultrasound probe 2 as the result of interference (combination) and are imaged as brightness points that reflect the interference.

In FIG. 9A, the imaging frequency is set to f, the scattered waves SWa, SWb in the same phase interfere with each other, and the interference wave IW1 is generated. The distance 2X between the scattered waves SWa and SWb is determined such that the scattered waves SWa, SWb combine (have the same phase) with each other in the interference wave IW1. Accordingly, the interference wave IW1 has the greatest amplitude (i.e., highest brightness) at the position shown in FIG. 9A.

In FIG. 9B, the scattered waves SWa, SWb in opposite phases interfere with each other, and the interference wave IW2 is generated. The distance 2X between the scattered waves SWa and SWb is determined such that the scattered waves SWa, SWb offset each other (have opposite phases) in the interference wave IW2. Thus, the amplitudes (image brightness) of the interference wave IW2 are largely different from that of the interference wave IW1, depending on the phase relation between two waves in interference (relation between the distance 2X and the wavelength (pulse width p)).

In FIG. 9C, the imaging frequency is lower than f, the scattered waves SWa, SWb having opposite phases interfere with each other, and the interference wave IW3 is generated. The distance 2X corresponding to the interference wave IW3 is the same as the distance 2X corresponding to the interference wave IW1, but the imaging frequency in FIG. 9C is lower than the frequency f. Accordingly, the scattered waves SWa, SWb offset each other. The lowest brightness position of the interference wave IW3 is the same as the highest brightness position of the interference wave IW1. As shown above, when the distance 2X is unchanged, the combination/offset in the interference wave changes depending on the change in the imaging frequency. Therefore, the brightness correlation at the same position is low.

Next, reception of scattered waves from sparse scatter sources is described. FIG. 10A shows an ultrasound image that includes less scatter virtual images (virtual images of scatter sources caused by scattered waves). FIG. 10B shows an ultrasound image that includes more scatter virtual images. When these images are compared, the ultrasound image in FIG. 10A delineates the dark parts well, whereas the ultrasound image in FIG. 10B poorly delineates the dark parts. It is therefore preferable that scatter virtual images be restrained.

As shown in FIG. 11, consider a case where the transmission wave (ultrasound beam) is transmitted toward the subject by the ultrasound probe 2 and scattered by scatter sources SC1, SC2, SC3 in the medium of the subject; and the scattered waves are received as reception waves by the ultrasound probe 2. The transmission wave from the ultrasound probe 2 passes along the center sound line A1 (first scanning) toward the transmission focal point F1. The arrows from the combined wave surface TW for transmission of the transmission wave indicates the motion of the combined wave.

It is known that, when a scatter source (scatterer) is smaller than the ultrasound wavelength, the small scatterer has a reflective power proportional to the fourth power of the frequency (see Ultrasound technology manual (newly revised edition), Junichi SANEYOSHI et al, 1978). Therefore, when the frequency of the transmitted ultrasound changes, the the scatter source scatters the ultrasound differently, so that the course of the scattered ultrasound (scattered wave) changes. In FIG. 11, the course of high-frequency ultrasound corresponding to the transmitted ultrasound from the ultrasound probe 2 is represented by a dash-dot-dash-dot arrow as the high-frequency scatter course; the course of medium-frequency ultrasound corresponding to the transmitted ultrasound is represented by a dash-dot-dot-dash arrow as the medium-frequency ultrasound scatter course; and the course of low-frequency ultrasound corresponding to the transmitted ultrasound is represented by a solid arrow as the low-frequency scatter course.

Assume that the transmitted ultrasound having a high frequency is scattered by the scatter source SC1; the transmitted ultrasound having a medium frequency is scattered by the scatter source SC2; the transmitted ultrasound having a low frequency is scattered by the scatter source SC3; and these scattered waves SC1, SC2, SC3 are received by the transducer 2a corresponding to the position of the center sound line A1. The received ultrasound including scattered waves yields an ultrasound image that shows a virtual image V1 of the scatter source SC1, a virtual image V2 of the scatter source SC2, and a virtual image V3 of the scatter source SC3. The positions of the virtual images V1, V2, V3 in the depth direction are different from each other. Therefore, when the ultrasound frequency is different, the positional correlation among the virtual images caused by the scatter sources is low. Regarding virtual images caused by sidelobe, the pitch of the Sinc function changes owing to the change in the ultrasound frequency, so that the virtual images cause by sidelobe also have low positional correlation.

In view of the above, multiplication is performed as the arithmetic operation among multiple ultrasound images of different imaging frequencies (imaging signals of ultrasound images). More specifically, brightness values corresponding to the same pixel position in the respective ultrasound images are multiplied. The ultrasound image (imaging signal of the ultrasound image) generated by the multiplication retains brightness values of pixels based on reflected waves having high brightness correlation at the same position, while restraining (depicting as dark parts) brightness values of pixels based on scattered waves having low brightness correlation at the same position.

Next, the operation of the diagnostic ultrasound apparatus 100A is described with reference to FIG. 12 to FIG. 19. FIG. 12 is a flowchart of a first ultrasound-image display process. FIG. 13 shows ultrasound images I1 to I4, an arithmetically-processed image I5, and a simple average image I6. FIG. 14A shows pixel values of a predetermined distance including the highest brightness point of a wire target in the ultrasound image I1 shown in FIG. 13. FIG. 14B shows pixel values of the predetermined distance including the highest brightness point of a wire target in the ultrasound image I2 shown in FIG. 13. FIG. 14C shows pixel values of the predetermined distance including the highest brightness point of the wire target in the arithmetically-processed image I5 shown in FIG. 13. FIG. 15 shows ultrasound images I11 to I14, binarized images I21 to I24, an arith-metically-processed image I15, and a binarized arithmeti-cally-processed image I25. FIG. 16 shows an example of a look up table (LUT). FIG. 17 shows the arithmetically-processed image I15 and the binarized arithmetically-pro-cessed image I25 shown in FIG. 15 and the LUT-converted arithmetically-processed image I35 and the binarized arith-metically-processed image I45. FIG. 18 shows side-by-side display of the ultrasound image I11 and the arithmetically-processed image I15 shown in FIG. 15. FIG. 19 shows side-by-side display of the arithmetically-processed image I15 shown in FIG. 15 and the difference image I51.

The first ultrasound-image display process executed by the diagnostic ultrasound apparatus 100A is described with reference to FIG. 12. In the first ultrasound-image display process, the arithmetically-processed imaging signal is gen-erated on the basis of imaging signals of different ultrasound images corresponding to different imaging conditions, and the arithmetically-processed image and so forth are dis-played.

The controller 19A of the diagnostic ultrasound apparatus 100A receives beforehand inputs of various setting infor-mation for displaying ultrasound images from the user (e.g., doctor, sonographer) via the operation receiver 11 and stores the received setting information in the RAM of the control-ler 19A or a not-illustrated storage. The input setting infor-mation includes: information regarding the gradation adjust-ment process to be performed on the arithmetically-processed image (arithmetically-processed imaging signal); information regarding whether the arithmetically-processed image and the normal image are displayed simultaneously; information regarding a difference image is generated on the basis of the arithmetically-processed image and the normal image; information regarding whether the difference image is displayed; and information regarding whether the index value based on the difference image is generated.

The controller 19A of the diagnostic ultrasound apparatus 100A performs the first ultrasound-image display process in accordance with the first ultrasound-image display program stored in the ROM, in response to receiving an instruction to perform the first ultrasound-image display process by the user via the operation receiver 11, for example. The flow-chart of FIG. 12 to be described shows the flow of generating and displaying one-frame ultrasound image data. Practically, multiple pieces of ultrasound image data may be generated and displayed sequentially in real time as a live display of ultrasound images, for example. The same applies to FIG. 21, FIG. 23, and FIG. 26 to be described later.

In FIG. 12, the controller 19A firstly causes the transmit-ter 12 to generate a drive signal containing three fundamen-tals shown in FIG. 4A for pulse inversion for tissue har-monic imaging. The controller 19A causes the ultrasound probe 2 to transmit ultrasound corresponding to the drive signal to the subject (Step S11).

The controller 19A causes the receiver 13 to receive reflected ultrasound, which is transmitted in Step S11 and reflected/scattered in the subject, and to generate a reception signal. The controller 19A also causes the sound-ray signal generator 14A to perform amplification, A/D conversion, and phase-and-sum process on the generated reception sig-nal to generate a sound ray signal containing harmonics of the three basic fundamentals (Step S12). The controller 19A causes the harmonic component extractor 14a to extract the harmonic components by pulse inversion from the sound ray signal generated in Step S12 and to generate the sound ray signal of the extracted harmonic components (Step S13).

The controller 19A causes the imaging signal extractor 15a1 to generate the first imaging signal under the first imaging condition (Step S14). Specifically, the imaging signal extractor 15a1 passes the sound ray signal generated in Step S13 through the first band-pass filter that passes a predetermined frequency band as the first imaging condi-tion.

At the same time with Step S14, the controller 19A causes the imaging signal extractor 15a2 to generate the second imaging signal under the second imaging condition (Step S15). Specifically, the imaging signal extractor 15a2 passes the sound ray signal generated in Step S13 through the second band-pass filter that passes a predetermined fre-quency band as the second imaging condition. Similarly, at the same time with Step S14, the controller 19A causes the imaging signal extractors 15a3 to 15a(n−1) to generate the third to (n−1)th imaging signals. At the same time with Step S14, the controller 19A causes the imaging signal extractor 15an to generate the n-th imaging signal under the n-th imaging condition (Step S16). Specifically, the imaging signal extractor 15an passes the sound ray signal generated in Step S13 through the n-th band-pass filter that passes a predetermined frequency band as the n-th imaging condi-tion.

The controller 19A causes the imaging signal calculator 15b to perform the arithmetic operation among the first to n-th imaging signals generated in Step S14 to S16 to generate an arithmetically-processed imaging signal (Step S17). Herein, the arithmetic operation is the multiplication of first to n-th imaging signals.

The controller 19A refers to the setting information stored in the RAM or the not-illustrated storage and causes the imaging signal calculator 15b to perform the gradation adjustment process on the arithmetically-processed imaging signal generated in Step S17 (Step S18). The gradation adjustment process corresponds to the setting information. The gradation adjustment process is a power root calculation process or an LUT conversion process, for example.

On the basis of the setting information, which is referred to in Step S18, the controller 19A determines whether or not to display the arithmetically-processed image and the nor-mal image simultaneously (Step S19). When determining that the arithmetically-processed image and the normal image are displayed simultaneously (Step S19: YES), the controller 19A causes the DSC 16 to generate (i) the first image data (normal image data) based on the first imaging signal (normal imaging signal) generated in Step S14 and (ii) the arithmetically-processed image data based on the arithmetically-processed imaging signal generated in Step S18 after the gradation adjustment process. The controller 19A causes the display image composer 17*a* to generate combined image data in which the normal image and the arithmetically-processed image are arranged side by side, on the basis of the normal image data and the arithmetically-processed image data (Step S20).

On the basis of the setting information, which is referred to in Step S18, the controller 19A determines whether or not to generate the difference image (Step S21). When the arithmetically-processed image and the normal image are not displayed simultaneously (Step S19: NO), the controller 19A proceeds to Step S21. When determining to generate the difference image (step S21: YES), the controller 19A causes the imaging signal analyzer 15*c* to generate the difference imaging signal (Step S22). The imaging signal analyzer 15*c* generates the difference imaging signal by obtaining the difference between the first imaging signal (normal imaging signal) generated in Step S14 and the arithmetically-processed imaging signal generated in in Step S18 after the gradation adjustment process.

On the basis of the setting information, which is referred to in Step S18, the controller 19A determines whether or not to display the difference image (Step S23). In step S23, the controller 19A determines "YES" when at least Step S22 is executed. When determining not to generate the difference image (Step S21: NO), the controller 19A proceeds to Step S23. When determining to display the difference image (Step S23: YES), the controller 19A causes the DSC 16 to generate (i) the arithmetically-processed image data based on the arithmetically-processed imaging signal generated in Step S18 after the gradation adjustment process and (ii) the difference image data based on the difference imaging signal generated in Step S22. The controller 19*a* then causes the image analysis indication value generator 17*b* to color the generated difference image data to generate the difference image data for display. the controller 19A also causes the display image composer 17*a* to generate combined image data in which the arithmetically-processed image and the difference image are arranged side by side, on the basis of the arithmetically-processed image data and the difference image data for display (Step S24).

On the basis of the setting information, which is referred to in Step S18, the controller 19A determines whether or not to display the index value based on the difference image (Step S25). In step S25, the controller 19A determines "YES" when at least Step S22 is executed. When determining not to display the difference image (Step S23: NO), the controller 19A proceeds to Step S25. When determining to display the index value based on the difference image (Step S25), the controller 19A causes the imaging signal analyzer 15*c* to calculate the index value based on the difference image, on the basis of the difference imaging signal generated in Step S22 (Step S26). The controller 19A causes the DSC 16 to generate the arithmetically-processed image data from the arithmetically-processed imaging signal generated in Step S18 after the gradation adjustment process; the controller 19A causes the image analysis indication value generator 17*b* to generate the index value based on the difference image for display from the index value based on the generated difference image; and the controller 19 causes the display image composer 17*a* to generate combined image data in which the arithmetically-processed image and the index value based on the difference image for display are arranged, on the basis of the arithmetically-processed image data and the index value based on the difference image for display (Step S27).

After performing Step S27 or when determining not to display the index value based on the difference image (Step S25; NO), the controller 19A displays, on the display 18, the combined image of the combined image data generated in Step S20, S24, S27 (Step S28). The controller 19A then ends the first ultrasound-image display process. When Step S19, S21, S23, S25 are all "NO" in Step S28, the controller 19A causes the DSC 16 to generate the arithmetically-processed image data on the basis of the arithmetically-processed imaging signal generated in Step S18 after the gradation adjustment process, and displays the generated arithmetically-processed image on the display 18.

Next, examples of images generated in the first ultrasound-image display process are described with reference to FIG. 13 to FIG. 19.

The diagnostic ultrasound apparatus 100A obtains ultrasound images of ultrasound image data as shown in FIG. 13 by scanning a phantom in which a wire target is placed as the subject. Herein, n=4. These ultrasound images are described. In steps S14 to S16 of the first ultrasound-image display process, the diagnostic ultrasound apparatus 100A generates ultrasound images I1, I2, I3, I4 that correspond to different frequency bands as imaging conditions. The ultrasound image I1 corresponds to the band B1 (full band) in FIG. 4B. The ultrasound image I2 corresponds to the band B2 in FIG. 4B. The ultrasound image I3 corresponds to the band B3 in FIG. 4B. The ultrasound image I4 corresponds to the band B4 in FIG. 4B. To the left of the respective ultrasound images, a grayscale chart of brightness values is shown. The chart shows gradation of brightness values by values of 0 to 255, for example.

In Step S17, the diagnostic ultrasound apparatus 100A performs multiplication as the arithmetic operation among the ultrasound images I1, I2, I3, I4 (among the imaging signals of the ultrasound images I2, I2, I3, I4). In step S18, the diagnostic ultrasound apparatus 100A performs the fourth root calculation process on the multiplication product as the gradation adjustment process. The diagnostic ultrasound apparatus 100A thus generates the arithmetically-processed image I5. The ultrasound image I1 includes less dark regions as compared with the ultrasound images I2, I3, I4. Further, in the arithmetically-processed image I5, scatter components are restrained and dark regions are increased as compared with in the ultrasound image I1. Accordingly, the wire target (reflection components) is more visible in the arithmetically-processed image I5.

FIG. 14A shows pixel values of a predetermined distance (30 pixels) including the highest brightness point of the wire target in the ultrasound image I1. In the graph of FIG. 14A, the horizontal axis indicates the distance (pixels) from a predetermined position in the depth direction, and the vertical axis indicates the brightness values. The same applies to the graphs shown in FIG. 14B and FIG. 14C. FIG. 14B shows the graph of brightness values of the predetermined distance (30 pixels) including the highest brightness point of the wire target in the ultrasound image I2. FIG. 14C shows the graph of brightness values of the predetermined distance (30 pixels) including the highest brightness point of the wire target in the arithmetically-processed image I5.

In the graphs of FIG. 14A to FIG. 14C, the highest brightness point, at which the brightness value is the maximum, corresponds to the center position of the wire target. The narrower the width of the part tracing the peak of brightness values is, the higher the range resolution of the image is. As compared with the ultrasound image I1 corresponding to the full band B1, the ultrasound image I2 corresponding to the band B2 narrower than the full band has a lower range resolution. The arithmetically-processed image I5, on the other hand, has the range resolution as high as the range resolution of the ultrasound image I1.

FIG. 13 shows the simple average image I6 generated by simply averaging the brightness values of the respective corresponding pixels among the ultrasound images I1 to I4. In the simple average image I6, high brightness values of pixels are smoothed and the low brightness parts are filled (not clear). The simple average image I6 includes less dark regions, does not sufficiently restrain scatter components, and is affected by the low resolution. On the other hand, the arithmetically-processed image I5, which is obtained through the multiplication and the power root calculation process without complicated image processing, successfully restrains brightness values of scatter components (matrix parts) while little decreasing the range resolution for the wire target, as compared with the simple average image I6. The ultrasound images I1 to I4, the arithmetically-processed image I5, and the simple average image I6 show the depth of around 1 centimeter, wherein the arithmetically-processed image I5 conspicuously exhibits the effect of restraining brightness of scatter components while little decreasing the range resolution.

Next, ultrasound images of ultrasound image data shown in FIG. 15 are described. The diagnostic ultrasound apparatus 100A obtains the ultrasound images shown in FIG. 14 by scanning the pork as the subject. Herein, n=4. In steps S14 to S16 of the first ultrasound-image display process, the diagnostic ultrasound apparatus 100A generates ultrasound images I11, I12, I13, I14 that correspond to different frequency bands as imaging conditions. The ultrasound image I11 corresponds to the band B1 (full band) in FIG. 4B. The ultrasound image I12 corresponds to the band B2 in FIG. 4B. The ultrasound image I13 corresponds to the band B3 in FIG. 4B. The ultrasound image I14 corresponds to the band B4 in FIG. 4B.

In Step S17, the diagnostic ultrasound apparatus 100A performs multiplication as the arithmetic operation among the ultrasound images I11, I12, I13, I14 (among the imaging signals of the ultrasound images I11, I12, I13, I14). In step S18, the diagnostic ultrasound apparatus 100A performs the fourth root calculation process on the multiplication product as the gradation adjustment process. Thus, the arithmetically-processed image I15 is generated. The ultrasound image I11 includes less dark regions as compared with the ultrasound images I12, I13, I14. In the arithmetically-processed image I15, scatter components are restrained and dark regions are increased, so that the reflection components such as fascias are more visible as compared with the ultrasound image I11.

I21 is a binarized image that is generated by binarizing the ultrasound image I11 with respect to a predetermined brightness value threshold. The binarized images I21, I22, I23, I24 and the binarized arithmetically-processed image I25 are generated by binarizing the ultrasound images I11, I12, I13, I14 and the arithmetically-processed image I15, respectively with respect to the threshold used for the binarized image I21. The arithmetically-processed image I15 and the binarized arithmetically-processed image I25 restrain the brightness (scatter components) between fascias while improving the continuity of fascias (reflection components) in the subject. Thus, scatter components can be sufficiently restrained (e.g., intramuscular fat of an aged individual) by generating an image through the arithmetic operation among multiple ultrasound images of different frequency bands.

Next, a case of performing the LUT conversion is explained. The diagnostic ultrasound apparatus 100A performs the LUT conversion on the ultrasound images of ultrasound image data obtained by scanning the pork as the subject. Herein, N=4. For the LUT conversion, the LUT shown in FIG. 16 is used. The LUT shows output signals (%) with respect to input signals (%). According to the LUT, the output signal is 0% when the input signal is 0 to 4%, and the input signal between 4 to 100% is converted to the output signal between 0 to 100%.

As with FIG. 15, in Steps S14 to S16 of the first ultrasound-image display process, the diagnostic ultrasound apparatus 100A generates the ultrasound images I11, I12, I13, I14. In Step S17, the diagnostic ultrasound apparatus 100A performs multiplication as the arithmetic operation among the ultrasound images I11, I12, I13, I14 (among the imaging signals of the ultrasound images I11, I12, I13, I14). In step S18, the diagnostic ultrasound apparatus 100A performs the fourth root calculation process on the multiplication product as the gradation adjustment process. Thus, the arithmetically-processed image I15 is generated. FIG. 17 shows the arithmetically-processed image I15 and the binarized arithmetically-processed image I25.

In Steps S14 to S16 of the first ultrasound-image display process, the diagnostic ultrasound apparatus 100A generates the ultrasound images I11, I12, I13, I14 and performs the LUT conversion process on I11, I12, I13, I14 using the LUT in FIG. 16. In Step S17, the diagnostic ultrasound apparatus 100A performs multiplication as the arithmetic operation among the ultrasound images I11, I12, I13, I14 (among imaging signals thereof). In Step S18, the diagnostic ultrasound apparatus 100A performs the fourth root calculation process as the gradation adjustment process on the multiplication product. Thus, the arithmetically-processed image I35 is generated as shown in FIG. 17. The arithmetically-processed image I35 is further binarized to generate the binarized arithmetically-processed image I45 using the same threshold as the binarized arithmetically-processed image I25. As the pixel ratio data of the binarized arithmetically-processed image I25, the pixel ratio of dark (black) regions in the ultrasound image region is 18%. As the pixel ratio data of the binarized arithmetically-processed image I45, the pixel ratio of dark (black) regions in the ultrasound image region is 19%.

In the arithmetic operation, imaging signals may be used as they are. However, in order to improve the effect of restraining low-correlation signals, it is preferable that the LUT conversion be performed before the arithmetic operation. In the LUT conversion, the input signals equal to or less than a predetermined value is converted to 0% output signal. As compared with the arithmetically-processed image I15 and the binarized arithmetically-processed image I25, the arithmetically-processed image I35 and the binarized arithmetically-processed image I45 more restrain low-correlation signal regions (scatter components), so that high-correlation signal regions (reflection components) are more visible.

Next, a case of displaying the arithmetically-processed image and the normal image side by side is described. The diagnostic ultrasound apparatus 100A scans the pork as the subject to obtain ultrasound image data, and generates the arithmetically-processed image from ultrasound images corresponding to the ultrasound image data. Herein, n=4. The setting information regarding whether the arithmetically-processed image and the normal image are displayed simultaneously is stored beforehand on the basis of input operations by the user via the operation receiver 11.

As with in FIG. 15, the diagnostic ultrasound apparatus 100A generates the ultrasound images I11, I12, I13, I14 in Steps S14 to S16 of the first ultrasound-image display process. The diagnostic ultrasound apparatus 100A then performs multiplication as the arithmetic operation among the ultrasound images I11, I12, I13, I14 (among imaging signals of the ultrasound images I11, I12, I13, I14) in Step S17. The diagnostic ultrasound apparatus 100A then performs the fourth root calculation process on the multiplication product as the gradation adjustment process. Thus, the arithmetically-processed image I15 is generated.

In Step S19, the diagnostic ultrasound apparatus 100A determines that the normal image and the arithmetically-processed image are displayed simultaneously. In Step S20, the diagnostic ultrasound apparatus 100A generates the combined image data in which the ultrasound image I11 (normal image data) and the arithmetically-processed image I15 (arithmetically-processed image data) are arranged side by side in the horizontal direction. In Step S28, the diagnostic ultrasound apparatus 100A displays the combined image of the combined image data (the ultrasound image I11 and the arithmetically-processed image I15) on the display 18, as shown in FIG. 18. The side-by-side display allows the user to visually confirm the difference between the ultrasound image I11 (normal image) and the arithmetically-processed image I15 easily and correctly.

Next, a case of displaying the arithmetically-processed image and the difference image side by side is described. The diagnostic ultrasound apparatus 100A scans the pork (subject) to obtain ultrasound image data, and generates the arithmetically-processed image from ultrasound images corresponding to the ultrasound image data. Herein, n=4. The diagnostic ultrasound apparatus 100A stores beforehand the setting information regarding whether the difference image, which shows the difference between the normal image and the arithmetically-processed image, is generated and displayed, on the basis of input operations by the user via the operation receiver 11.

As with in FIG. 15, the diagnostic ultrasound apparatus 100A generates the ultrasound images I11, I12, I13, I14 in Steps S14 to S16 of the first ultrasound-image display process. The diagnostic ultrasound apparatus 100A then performs multiplication as the arithmetic operation among the ultrasound images I11, I12, I13, I14 (among imaging signals of the ultrasound images I11, I12, I13, I14) in Step S17. The diagnostic ultrasound apparatus 100A then performs the fourth root calculation process on the multiplication product as the gradation adjustment process. Thus, the arithmetically-processed image I15 is generated.

In Step S21, the diagnostic ultrasound apparatus 100A determines to generate the difference image as shown in FIG. 19. In Step S22, the diagnostic ultrasound apparatus 100A generates the difference image (difference imaging signal) on the basis of the difference between the ultrasound image I11 based on the normal image data and the arithmetically-processed image I15 based on the arithmetically-processed image data. In Step S23, the diagnostic ultrasound apparatus 100A determines to display the difference image. In Step S24, the diagnostic ultrasound apparatus 100A generates the normal image data for the ultrasound image I11 and the difference image data based on the difference between the arithmetically-processed image I15 and the difference image I51; colors the difference image data; and combines the normal image data and the colored difference image data to generate the combined image data. In Step S28, the diagnostic ultrasound apparatus 100A displays the combined image (the arithmetically-processed image I15 and the difference image I51) of the combined image data on the display 18. Herein, the colored difference image I51 is displayed as parametric display.

The difference image I51 consists of pixels each of which has a difference value between the corresponding brightness values at the same position in the ultrasound image I11 and the arithmetically-processed image I15. In the figure, colors of pixels constituting the difference image I51 vary from white, light gray, dark gray to black, so as to correspond to low difference values to high difference values. However, in the actually displayed difference image I51, pixels constituting the difference image I51 are colored by the coloring LUT conversion such that the colors of pixels vary from black, blue, green, yellow, to white so as to correspond to low difference values to high difference values, for example. The difference image colored with difference hues for parametric display allows the user to more easily grasp the range and frequency of pixels having the same brightness, as compared with the difference image colored only black and white based on the difference values. The difference image may be colored with other hues or may be displayed in black and white. Further, the difference image I51 may correspond to the region of interest input by the user via the operation receiver 11.

As described above, according to this embodiment, the diagnostic ultrasound apparatus 100A includes: the sound-ray signal generator 14A that generates a sound ray signal(s) based on a reception signal(s) obtained from the ultrasound probe 2 that transmits and receives ultrasound to and from the subject; imaging signal extractors 15a1 to 15an that generate first to n-th imaging signals by performing filtering on the sound ray signal using the first to n-th band pass filters that pass different bands (n bands); and the imaging signal calculator 15b that performs the arithmetic operation among the first to n-th imaging signals. By the arithmetic operation among the multiple ultrasound images corresponding to different imaging conditions (different frequency bands), the diagnostic ultrasound apparatus 100A can depict tissues (reflectors) with high resolution even when the subject includes many scatterers in the tissues, while restraining scattered acoustic noise. Thus, the diagnostic ultrasound apparatus 100A can achieve both the high resolution and the visibility of tissues.

Further, the imaging signal calculator 15b may multiply the first to n-th imaging signals as the arithmetic operation. The multiplication does not require any complicated image processing. The diagnostic ultrasound apparatus 100A can therefore depict the tissues (reflectors) in high resolution and restrain scattered acoustic noise while reducing processing loads.

Further, the imaging signal calculator 15b may perform the n-th root calculation process on the multiplied first to n-th imaging signals, "n" corresponding to the number of imaging signals. With the n-th root calculation process, the gradation adjustment process can be performed appropriately and relatively easily. When only multiplication is performed, the resulting ultrasound image may have low tissue visibility in which only the high-brightness parts are emphasized. The n-th root calculation process can prevent generation of such an ultrasound image.

Further, the imaging signal calculator 15b may perform the LUT conversion process on the arithmetically-processed imaging signal (arithmetically-processed first to n-th imaging signals). The LUT conversion process eliminates the need of individual arithmetic operations and allows an appropriate gradation adjustment process. When only multiplication is performed, the resulting ultrasound image may have low tissue visibility in which only the high-brightness parts are emphasized. The LUT conversion process can prevent generation of such an ultrasound image.

Further, the fractional bandwidth of −20 dB of the ultrasound probe 2 may be equal to or greater than 100%. If the fractional bandwidth of −20 dB of the ultrasound probe 2 is reduced, among multiple ultrasound images corresponding to different imaging conditions (frequency bands), the difference between high-brightness regions and low-brightness regions may not be obtained. When the fractional bandwidth of −20 dB is equal to or greater than 100%, the diagnostic ultrasound apparatus 100A can retain both the high resolution of the arithmetically-processed image and the tissue visibility by restraining scattered acoustic noise.

Further, the diagnostic ultrasound apparatus 100A may further include the transmitter 12 that generates a drive signal containing multiple fundamentals corresponding to different frequencies and outputs the generated drive signal to the ultrasound probe 2. The sound-ray signal generator 14A may generate the sound ray signal that contains harmonic components of multiple fundamentals. According to such a configuration, the resolution of the arithmetically-processed image can be further improved.

Further, the imaging signal calculator 15b converts brightness values equal to or less than a predetermined value of imaging signals to zero before the arithmetic operation is performed. Accordingly, low-correlation signal parts (scatter components) in the arithmetically-processed image can be further restrained, and high-correlation signal parts (reflection components) can be more visible.

Further, the diagnostic ultrasound apparatus 100A may include the display image composer 17a that displays the normal image and the arithmetically-processed image side by side simultaneously on the display 18, the normal image being based on the normal imaging signal on which the arithmetic operation is not performed, the arithmetically-processed image being based on the arithmetically-processed imaging signal. This allows the user to easily compare and view the normal image and the arithmetically-processed image.

Further, the diagnostic ultrasound apparatus 100A may include: the imaging signal analyzer 15c that generates the difference imaging signal corresponding to the difference image showing the difference between the normal image, which is based on the normal imaging signal on which the arithmetic operation is not performed, and the arithmetically-processed image, which is based on the arithmetically-processed imaging signal; and the image processor 17A (display image composer 17a) that displays the difference image on the display 18. This allows the user to view the difference between the normal image and the arithmetically-processed image for diagnosis.

Further, the image processor 17A (image analysis indication value generator 17b) may color the difference image and display the colored difference image on the display 18. This allows the user to view the colored difference image for diagnosis.

Further, the imaging signal analyzer 15c may calculate the index value based on the difference image. The image processor 17A (display image composer 17a) displays the index value based on the difference image on the display 18. This allows the user to view the index value based on the difference image for diagnosis.

Second Embodiment

The second embodiment of the present invention is described with reference to FIG. 20 to FIG. 21. FIG. 20 is a block diagram showing functional components of the diagnostic ultrasound apparatus 100B in the second embodiment. FIG. 21 is a flowchart of a second ultrasound-image display process.

Firstly, the entire configuration of the apparatus in this embodiment is described with reference to FIG. 20. As shown in FIG. 20, the diagnostic ultrasound apparatus 100B is used in the second embodiment. Elements of the diagnostic ultrasound apparatus 100B that are the same as that of the diagnostic ultrasound apparatus 100A in the first embodiment are denoted by the same reference numerals and not described. The aspects different from the first embodiment are described below.

The diagnostic ultrasound apparatus 100B includes the ultrasound diagnostic apparatus main body 1B and the ultrasound probe 2. The diagnostic ultrasound apparatus main body 1B includes the operation receiver 11, the transmitter 12, the receiver 13, the sound-ray signal generator 14A, the signal processor 15B, the DSC 16, the image processor 17B, the display 18, and the controller 19B.

The signal processor 15B includes the imaging signal extractors 15a1 to 15an. Under the control of the controller 19B, the DSC 16 performs envelope demodulation and logarithmic compression on the first to n-th imaging signals (sound ray signals) input from the imaging signal extractors 15a1 to 15an and further adjusts the dynamic range and the gain for brightness conversion. The DSC 16 further performs polar coordinate conversion and calculation for interpolation of display pixels as desired. The DSC 16 thus generates the first image data (normal image data) to the n-th image data as B-mode image data for display.

The image processor 17B is a circuit that processes the image data input by the DSC 16. The image processor 17B includes an image calculator 17c as a calculator; an image analyzer 17d as an analyzer; the display image composer 17a; and the image analysis indication value generator 17b.

Under the control of the controller 19B, the image calculator 17c performs multiplication as the arithmetic operation among the first to n-th image data input by the DSC 16 to generate the arithmetically-processed image data. Under the control of the controller 19B, the image calculator 17c further performs the gradation adjustment process on the generated arithmetically-processed image data.

Under the control of the controller 19B, the image analyzer 17d analyzes the arithmetically-processed image data generated by the image calculator 17c. The analysis includes a process of generating the difference image data of the difference image by calculating the difference between thee normal image data and the arithmetically-processed image data; and a process of generating the index value based on the difference image of the generated difference image data.

Under the control of the controller 19B, the display image composer 17a generates combined image data for display by combining at least two among the normal image data input by the DSC 16, the arithmetically-processed image data input by the image calculator 17c, the difference image data for display input by the image analysis indication value generator 17b, and the index value based on the difference image such that the display contents are displayed side by side.

Under the control of the controller 19B, the image analysis indication value generator 17b colors the difference image data input by the DSC 16 to generate the difference image data for display, and the image analysis indication value generator 17b further generates the index value based on the difference image for display from the index value based on the difference image input by the image analyzer 17*d*.

The configuration of the controller 19B is the same as that of the controller 19A in the first embodiment. The controller 19B centrally controls the operation of each component constituting the diagnostic ultrasound apparatus 100B. The ROM of the controller 19B stores a second ultrasound image display program for executing the second ultrasound image display process to be described later, instead of the first ultrasound image display program.

Next, the operation of the diagnostic ultrasound apparatus 100B is described with reference to FIG. 21. Specifically, the second ultrasound image display process performed by the diagnostic ultrasound apparatus 100B is described with reference to FIG. 21. In the second ultrasound image display process, the arithmetically-processed image data is generated on the basis of multiple pieces of ultrasound image data corresponding to different imaging conditions, and the arithmetically-processed image and so forth are displayed.

The controller 19B of the diagnostic ultrasound apparatus 100B receives beforehand inputs of various setting information for displaying ultrasound images from the user (e.g., doctor, sonographer) via the operation receiver 11 and stores the received setting information in the RAM of the controller 19B or a not-illustrated storage. The input setting information includes information regarding the gradation adjustment process to be performed on the arithmetically-processed image (arithmetically-processed image data), information regarding whether the arithmetically-processed image and the normal image are displayed simultaneously, information regarding whether the difference image is generated on the basis of the normal image and the arithmetically-processed image, information regarding whether the difference image is displayed, and information regarding whether the index value based on the difference image is generated.

The controller 19B of the diagnostic ultrasound apparatus 100B performs the second ultrasound-image display process in accordance with the second ultrasound image display program stored in the ROM in response to receiving an instruction to perform the second ultrasound-image display process by the user via the operation receiver 11, for example.

In FIG. 21, Steps S31 to S36 are the same as Steps S11 to S16 of the first ultrasound-image display process shown in FIG. 12. The controller 19B causes the DSC 16 to generate the first to n-th image data from the first to n-th imaging signals generated in Steps S34 to S36, and further causes the image calculator 17*c* to perform the arithmetic operation among the generated first to n-th image data to generate the arithmetically-processed image data (Step S37). The arithmetic operation performed here is multiplication of first to n-th image data (multiplication of brightness values of corresponding pixels at the same position among the images of the respective pieces of image data).

The controller 19B refers to the setting information stored in the RAM or the not-illustrated storage and, on the basis of the setting information, causes the image calculator 17*c* to perform the gradation adjustment process on the arithmetically-processed image data generated in Step S37 (Step S38).

Step S39 is the same as Step S19 in FIG. 12. When the arithmetically-processed image and the normal image are displayed simultaneously (Step S39: YES), the controller 19B causes the display image composer 17*a* to generate combined image data in which the normal image and the arithmetically-processed image are arranged side by side, on the basis of the normal image data (first image data) generated in Step S37 and the arithmetically-processed image data generated in Step S38 after the gradation adjustment process (Step S40).

Step S41 is the same as Step S21 in FIG. 12. When the difference image is generated (Step S41: YES), the controller 19B causes the image analyzer 17*d* to generate difference image data by calculating the difference between the normal image data (first image data) generated in Step S37 and the arithmetically-processed image data generated in step S38 after the gradation adjustment process (Step S42).

Step S43 is the same as Step S23 in FIG. 12. When the difference image is displayed (Step S43: YES), the controller 19B causes the image analysis indication value generator 17*b* to generate difference image data for display by coloring the difference image data generated in Step S42, and the controller 19B causes the display image composer 17*a* to generate combined image data in which the arithmetically-processed image and the difference image are arranged side by side, on the basis of the arithmetically-processed image data generated in Step S37 and the difference image data for display (Step S44).

Step S45 is the same as Step S25 in FIG. 12. When the index value based on the difference image is displayed (Step S45: YES), the controller 19B causes the image analyzer 17*d* to calculate the index value based on the difference image, on the basis of the difference image data generated in Step S42 (Step S46). The controller 19B causes the image analysis indication value generator 17*b* to generate the index value based on the difference image for display, on the basis of the index value based on the difference image, and the controller 19B causes the display image composer 17*a* to generate combined image data in which the arithmetically-processed image and the index value based on the difference image for display are arranged, on the basis of the arithmetically-processed image data generated in Step S38 and the index value based on the difference image for display (Step S47).

After performing Step S47 or when the index value based on the difference image is not displayed (Step S45: NO), the controller 19B displays, on the display 18, the combined image of the combined image data generated in Step S40, S44, S47 (Step S48). The controller 19B then ends the second ultrasound-image display process. When Step S39, S41, S43, S45 are all "NO" in Step S48, the controller 19B displays, on the display 18, the arithmetically-processed image of the arithmetically-processed image data generated in Step S38 after the gradation adjustment process.

As described above, according to the second embodiment, the imaging signals that are subjected to the arithmetic operation and so forth are image data. As with the first embodiment, by the arithmetic operation among the multiple ultrasound images corresponding to different imaging conditions (different frequency bands), the diagnostic ultrasound apparatus 100B can depict tissues (reflectors) in high resolution while restraining acoustic noise when the subject includes many scatterers in the tissues. Thus, the diagnostic ultrasound apparatus 100B can achieve both the high resolution and the visibility of tissues.

Third Embodiment

The third embodiment of the present invention is described with reference to FIG. 22 to FIG. 26. FIG. 22 is a block diagram showing functional components of the diagnostic ultrasound apparatus 100C in the third embodiment. FIG. 23 is a flowchart of a third ultrasound-image display process. FIG. 24 shows ultrasound images I61, I62, I63 subjected to different phase-and-sum conditions. FIG. 25 shows watershed division images I71, I72, I73 corresponding to the ultrasound images I61, I61, I63 in FIG. 24. FIG. 26 is a flowchart showing the fourth ultrasound-image display process.

Firstly, the configuration of the apparatus in this embodiment is described with reference to FIG. 22. As shown in FIG. 22, the diagnostic ultrasound apparatus 100C is used in the third embodiment. Elements of the diagnostic ultrasound apparatus 100C that are the same as that of the diagnostic ultrasound apparatus 100A in the first embodiment are denoted by the same reference numerals and not described. The aspects different from the first embodiment are described below.

The diagnostic ultrasound apparatus 100C includes the ultrasound diagnostic apparatus main body 1B and the ultrasound probe 2. The diagnostic ultrasound apparatus main body 1C includes the operation receiver 11, the transmitter 12, the receiver 13, the sound ray signal generator 14C, the signal processor 15C, the DSC 16, the image processor 17A, the display 18, and the controller 19C.

The receiver 13 receives reception signals (electric signals) that correspond to the first to N-th phase-and-sum conditions (N: a natural number equal to or greater than 2) from the ultrasound probe 2 under the control of the controller 19C. The first to N-th phase-and-sum conditions relate to phasing and summing the reception signals. For example, the conditions relate to the number of reception apertures (width of reception apertures) corresponding to the number of reception channels of the transducers 2a of the ultrasound probe 2, the set sound speed, and apodization. The drive signals generated by the transmitter 12 correspond to the first to N-th phase-and-sum conditions.

The sound ray signal generator 14C includes sound ray signal generators 14b1 to 14bN and the harmonic component extractor 14a. The sound ray signal generators 14b1 to 14bN each include an amplifier, an A/D converter circuit, and a phase-and-sum circuit. Under the control of the controller 19C, the sound ray signal generators 14b1 to 14bN generate the first to N-th sound ray signals (first to N-th sound ray data) from the reception signal received by the receiver 13 according to the first to N-th phase-and-sum conditions. For example, when the first phase-and-sum condition specifies that all of the reception apertures are used, the sound ray signal generator 14b1 generates the first sound ray signal from the reception signal according to the first phase-and-sum condition. Herein, the first sound ray signal is the normal sound ray signal for a normal image corresponding to the number of all-apertures for receiving all). The sound ray signal generator 14b1 may be configured to generate the normal image sound ray signal according to the normal phase-and-sum condition.

Under the control of the controller 19C, the harmonic component extractor 14a extracts harmonic components from the first to N-th sound ray signals output by the sound rays signal generators 14b1 to 14bN by pulse inversion.

The signal processor 15C includes imaging signal extractors 15a1 to 15an, the imaging signal calculator 15b, and the imaging signal analyzer 15c. In the fourth ultrasound-image display process to be described later, the imaging signal extractor 15a1 passes the first to N-th sound ray signals input by the harmonic component extractor 14a after extraction of harmonic components through the first band pass filter. The imaging signal extractor 15a1 thus extracts the (1-1)th to (N−1)th imaging signals from the first to N-th sound ray signals. The (1-1)th imaging signal is the normal imaging signal. Similarly, in the fourth ultrasound-image display process to be described later, the imaging signal extractors 15a2 to 15an extracts, from the first to N-th sound ray signals input by the harmonic component extractor 14a after extraction of harmonic components, the (1-2)th to (N−2)th imaging signals, . . . , and the (1-n)th to (N-n)th imaging signals, respectively.

In the fourth ultrasound-image display process to be described later, the imaging signal calculator 15b performs the arithmetic operation among the (1-1)th to (N-n) imaging signals, which are generated by the imaging signal extractors 15a1 to 15an for generating B-mode image data, to generate the arithmetically-processed imaging signal under the control of the controller 19C. In the third ultrasound-image display process to be described later, the imaging signal calculator 15b may perform the arithmetic operation among the first to N-th sound ray signals input by the harmonic component extractor 14a after extraction of harmonics to generate the arithmetically-processed imaging signal. The imaging signal calculator 15b further performs the gradation adjustment process on the generated cross-calculated imaging signal under the control of the controller 19C.

Under the control of the controller 19C, the imaging signal analyzer 15c analyzes the arithmetically-processed imaging signal obtained by the imaging signal calculator 15b and generates the difference imaging signal between the normal imaging signal and the arithmetically-processed imaging signal and the index value based on the difference image.

The configuration of the controller 19C is the same as that of the controller 19A in thee first embodiment. The controller 19C centrally controls the operation of each component constituting the diagnostic ultrasound apparatus 100C. The ROM of the controller 19C stores a third ultrasound image display program for executing the third ultrasound image display process to be described later and a fourth ultrasound image display program for executing the fourth ultrasound-image display process to be described later, instead of the first ultrasound image display program.

Next, the operation of the diagnostic ultrasound apparatus 100C is described with reference to FIG. 23 to FIG. 26. The third ultrasound-image display process executed by the diagnostic ultrasound apparatus 100C is described with reference to FIG. 23. In the third ultrasound-image display process, the arithmetically-processed imaging signal is generated from imaging signals of different ultrasound images corresponding to different phase-and-sum conditions, and the arithmetically-processed image and so forth are displayed.

The controller 19C of the diagnostic ultrasound apparatus 100C receives beforehand inputs of various setting information for displaying ultrasound images from the user (e.g., doctor, sonographer) via the operation receiver 11 and stores the received setting information in the RAM of the controller 19C or in a not-illustrated storage. The input setting information includes: information regarding the gradation adjustment process to be performed on the arithmetically-processed image (arithmetically-processed imaging signal); information regarding whether the arithmetically-processed image and the normal image are displayed simultaneously; information regarding a difference image is generated on the basis of the arithmetically-processed image and the normal image; information regarding whether the difference image is displayed; and information regarding whether the index value based on the difference image is generated.

The controller 19C of the diagnostic ultrasound apparatus 100C performs the third ultrasound-image display process in response to receiving an instruction to perform the third ultrasound-image display process by the user via the operation receiver 11, for example.

In FIG. 23, Step S51 is the same as Step S11 of the first ultrasound-image display process shown in FIG. 12. The controller 19C causes the receiver 13 to receive the reflected ultrasound and the scattered ultrasound, which are transmitted in Step 11 and reflected/scattered in the subject, and to generate the reception signal (Step S52).

The controller 19C causes the sound ray signal generator 14b1 to perform amplification, A/D conversion, and phase-and-sum process on the reception signal generated in Step S52 according to the first phase-and-sum condition, thereby generating the first sound ray signal that contains harmonic components of the three fundamentals (Step S53). The controller 19C causes the harmonic component extractor 14a to extract harmonic components from the first sound ray signal generated in Step S53 by pulse inversion to generate the first sound ray signal of the extracted harmonic components (Step S54). The controller 19C causes the signal processor 15C to generate the first imaging signal on the basis of the first sound ray signal generated in Step S54 (Step S55).

At the same time with Steps S53 to S55, the controller 19C causes the sound ray signal generator 14b2 to perform amplification, A/D conversion, and phase-and-sum process on the reception signal generated in Step S52 according to the second phase-and-sum condition, thereby generating the second sound ray signal that contains harmonic components of the three fundamentals (Step S56). The controller 19C causes the harmonic component extractor 14a to extract harmonic components from the second sound ray signal generated in Step S56 by pulse inversion to generate the second sound ray signal of the extracted harmonic components (Step S57). The controller 19C causes the signal processor 15C to generate the second imaging signal on the basis of the second sound ray signal generated in Step S57 (Step S58).

Similarly, the controller 19C causes the sound ray signal generators 14b3 to 14b(N−1), the harmonic component extractor 14a, and the signal processor 15C to generate the third to (N−1)th imaging signals. At the same time with Steps S53 to S55, the controller 19C causes the sound ray signal generator 14bN to perform amplification, A/D conversion, and phase-and-sum process on the reception signal generated in Step S52 according to the N-th phase-and-sum condition, thereby generating the N-th sound ray signal that contains harmonic components of the three fundamentals (Step S59). The controller 19C causes the harmonic component extractor 14a to extract harmonic components from the N-th sound ray signal generated in Step S59 by pulse inversion to generate the N-th sound ray signal of the extracted harmonic components (Step S60). The controller 19C causes the signal processor 15C to generate the N-th imaging signal on the basis of the N-th sound ray signal generated in Step S60 (Step S61).

The controller 19C causes the imaging signal calculator 15b to perform the arithmetic operation among the first to N-th imaging signals generated in Steps S55, S58, S61 to generate the arithmetically-processed imaging signal (Step S62). Herein, the arithmetic operation is the multiplication of first to N-th imaging signals. Steps S63 to S73 are the same as Steps S18 to S28 in FIG. 12.

Next, examples of images generated in the third ultrasound-image display process are described with reference to FIG. 24 and FIG. 25.

The diagnostic ultrasound apparatus 100A obtains ultrasound images of ultrasound image data as shown in FIG. 24 by scanning a phantom in which a wire target is placed as the subject. Herein, N=3. In steps S55, S58, S61 of the third ultrasound-image display process, the diagnostic ultrasound apparatus 100C generates first to third imaging signals for the ultrasound images I61, I62, I63 that correspond to different phase-and-sum conditions.

The ultrasound image I61 is based on the sound ray signal obtained by the phase-and-sum process using all the reception apertures of the ultrasound probe 2 as the first phase-and-sum condition. The ultrasound image I62 is based on the sound ray signal obtained by the phase-and-sum process using two-third ($\frac{2}{3}$) of all the reception apertures of the ultrasound probe 2 as the second phase-and-sum condition, which is more limited than the first phase-and-sum condition. The ultrasound image I63 is based on the sound ray signal obtained by the phase-and-sum process using one-third ($\frac{1}{3}$) of all the reception apertures of the ultrasound probe 2 as the second phase-and-sum condition, which is more limited than the second phase-and-sum condition. The ultrasound images I61, I62, I63 show that the degree of interference among reception channels change depending on the number of reception apertures and that the speckle pattern (interference pattern) changes. According to the ultrasound images I61, I62, I63, when the phase-and-sum condition (the number of reception apertures) is changed, the brightness correlation at the same position of reflection components of the wire target is high. On the other hand, the brightness correlation at the same positions of scatter components is low because the granularity of matrix parts (interference regions) changes mainly in the bearing direction and the positions of low brightness parts change. Therefore, as with the arithmetically-processed image in the first embodiment generated by performing the arithmetic operation among multiple ultrasound images corresponding to different imaging conditions (different frequency bands), the arithmetically-processed image generated by performing the arithmetic operation among multiple ultrasound images corresponding to different phase-and-sum conditions shows the reflector (reflection components) in high resolution while suppressing scatterers (scatter components).

In FIG. 25, the watershed division images I71, I72, I73 depict low image brightness parts (low brightness parts). The watershed division images I71, I72, I73 are obtained by performing the watershed division process on the ultrasound images I61, I62, I63 under the same condition. As shown by the watershed division images I71, I72, I73, the low image brightness points (black lines in I71, I72, I73) change according to the change in the number of reception apertures. The above shows that the arithmetically-processed image generated from the ultrasound images I61, I62, I63 corresponding to different phase-and-sum conditions can efficiently suppress scatter components while retaining reflection components.

The fourth ultrasound-image display process executed by the diagnostic ultrasound apparatus 100C is described with reference to FIG. 26. In the fourth ultrasound-image display process, the arithmetically-processed imaging signal is generated on the basis of imaging signals of different ultrasound images corresponding to different imaging conditions and different phase-and-sum conditions, and the arithmetically-processed image and so forth are displayed.

The controller 19C of the diagnostic ultrasound apparatus 100C receives beforehand inputs of various setting information for displaying ultrasound images from the user (e.g., doctor, sonographer) via the operation receiver 11 and stores the received setting information in the RAM of the controller 19C or in a not-illustrated storage. The input setting information includes: information regarding the gradation adjustment process to be performed on the arithmetically-processed image (arithmetically-processed imaging signal); information regarding whether the arithmetically-processed image and the normal image are displayed simultaneously; information regarding a difference image is generated on the basis of the arithmetically-processed image and the normal image; information regarding whether the difference image is displayed; and information regarding whether the index value based on the difference image is generated.

The controller 19C of the diagnostic ultrasound apparatus 100C performs the fourth ultrasound-image display process in accordance with the fourth ultrasound-image display program stored in the ROM, in response to receiving an instruction to perform the fourth ultrasound-image display process by the user via the operation receiver 11, for example.

In FIG. 26, Steps S81 to S84 are the same as Steps S51 to S54 of the third ultrasound-image display process shown in FIG. 23. The controller 19C causes the imaging signal extractor 15a1 to perform the first band-pass filtering on the first sound ray signal generated in Step S84 to generate the (1-1)th imaging signal (normal imaging signal) (Step S85). In the first band-pass filtering, the first band-pass filter passes a predetermined frequency band as the first imaging condition. Similarly, at the same time with Step S85, the controller 19C causes the imaging signal extractors 15a2 to 15a(n−1) to generate the (1-2)th to the 1−(n−1)th imaging signals. At the same time with Step S85, the controller 19C causes the imaging signal extractor 15an to perform the n-th band-pass filtering on the first sound ray signal generated in step S84 to generate the (1-n)th imaging signal (Step S86). In the n-th band-pass filtering, the n-th band pass filter passes a predetermined frequency band as the n-th imaging condition.

Similarly, at the same time with Steps S83 to S86, the controller 19C causes the sound ray signal generators 14b2 to 14b(N−1), the harmonic component extractor 14a, and the imaging signal extractors 15a1 to 15an to generate the (2-1)th to (2−n)th imaging signals, . . . , the (N−1)−1th to the (N−1)−n imaging signals.

Steps S87, 88 are the same as Steps S59, 60 in FIG. 23. The controller 19C causes the imaging signal extractor 15a1 to perform the first band-pass filtering on the N-th sound ray signal generated in Step S88 to generate the (N−1)th imaging signal (Step S89). In the first band pass filtering, the first band pass filter passes a predetermined frequency band as the first imaging condition. Similarly, at the same time with Step S89, the controller 19C causes the imaging signal extractors 15a2 to 15a(n−1) to generate the (N−2)th to the N−(n−1)th imaging signals. At the same time with Step S89, the controller 19C causes the imaging signal extractor 15an to perform the N-th band-pass filtering on the N-th sound ray signal generated in Step S88 to generate the (N−n) imaging signal (Step S90). In the n-th band pass filtering, the n-th band pass filter passes a predetermined frequency band as the n-th imaging condition.

The controller 19C causes the imaging signal calculator 15b to perform the arithmetic operation among the (1-1)th to (N-n)th imaging signals generated in Steps S85 . . . S86 . . . S89 . . . S90 to generate the arithmetically-processed imaging signal (Step S91). Herein, the arithmetic operation is the multiplication of the (1-1)th to (N-n)th imaging signals. Steps S92 to S102 are the same as Steps S63 to S73 in FIG. 23.

As described above, according to the third embodiment, the diagnostic ultrasound apparatus 100C includes: the sound-ray signal generators 14b1 to 14bN that perform the phase-and-sum process on the reception signal according to different phase-and-sum conditions and generates multiple (N) sound ray signals (first to N-th sound ray signals), the reception signal being obtained from the ultrasound probe 2 that transmits and receives ultrasound to and from the subject; and the imaging signal calculator 15b that performs the arithmetic operation among the first to N-th imaging signals that are based on the first to N-th sound ray signals. These functions correspond to the third ultrasound image display process. By the arithmetic operation among multiple ultrasound images corresponding to different phase-and-sum conditions, the diagnostic ultrasound apparatus 100C can depict tissues (reflectors) in high resolution while restraining scattered acoustic noise when the subject includes many scatterers in the tissues. Thus, the diagnostic ultrasound apparatus 100C can achieve both the high resolution and the visibility of tissues.

The diagnostic ultrasound apparatus 100C further includes the imaging signal extractors 15a1 to 15an that perform filtering for passing different multiple (n) frequency bands on the multiple (N) sound ray signals (first to N-th sound ray signals) to generate the (1-1)th to (N-n)th imaging signals. By the arithmetic operation among the multiple ultrasound images corresponding to different imaging conditions (different frequency bands) and different phase-and-sum conditions, the diagnostic ultrasound apparatus 100C can depict tissues (reflectors) with high resolution while restraining scattered acoustic noise when the subject includes many scatterers in the tissues. Thus, the diagnostic ultrasound apparatus 100C can achieve both the high resolution and the visibility of tissues.

In the above description, the ROM is used as a computer-readable medium that stores the programs of the present invention. However, the computer readable medium is not limited to the ROM. As other computer-readable storage media, a nonvolatile memory, such as a flash memory, and a portable storage medium, such as a CD-ROM, can also be used. Further, a carrier wave may be used as a medium to provide data of the programs of the present invention via a communication line.

The embodiments described above are preferred examples of the diagnostic ultrasound apparatus and the storage medium of the present invention and does not limit the present invention. For example, at least two among the first to third embodiments may be combined. Specifically, the second and third embodiments may be combined. In the case, in the diagnostic ultrasound apparatus 100C, the image processor 17A includes the image calculator 17c and the image analyzer 17d; the controller 19C causes the sound ray signal generator 14C to generate the first to N-th imaging signals; the controller 19C causes the imaging signal extractors 15a1 to 15an to generate the (1-1)th to (N-n)th imaging signals; the controller 19C causes the image calculator 17c to perform the arithmetic operation among the (1-1)th to (N-n)th image data obtained from the DSC 16 to generate arithmetically-processed image data; and the controller 19C causes the image analyzer 17d to analyze the arithmetically-processed image data (generate difference image data and the index value based on the difference image).

Further, in the above first to third embodiments, the signal processor 15A/15B/15C and the image processor 17A/17B may perform processing in units of frames or in units of sound rays.

Further, in the above first to third embodiments, the arithmetic operation is multiplication of ultrasound images (imaging signals (sound ray signals) or multiple pieces of image data). For example, the arithmetic operation among ultrasound images may be other than multiplication. The arithmetic operation may be the operation of obtaining arithmetically-processed brightness values by utilizing differences in image brightness correlation. Specifically, for m ultrasound images (m: a natural number equal to or greater than 2) generated under different imaging conditions and/or different phase-and-sum conditions, variation of brightness values at each pixel coordinate (x, y) in the respective ultrasound images (L1, L2, L3, . . . , Lm) is calculated as the variance V, and the reciprocal of V is multiplied by the average of brightness values LA, for example. Such a method can also yield an arithmetically-processed image (imaging signal (sound ray signal) or image data) that have arithmetically-processed brightness values reflecting variation levels.

The above first to third embodiments are intended for harmonic imaging mode, wherein the transmitter 12 of the diagnostic ultrasound apparatus 100A/100B/100C generates a drive signal for pulse inversion; and the sound-ray signal generator 14A/14C generates a sound ray signal for B-mode image for pulse inversion. However, the present invention is not limited to this. Other embodiments may be intended for harmonic imaging mode in which harmonics are extracted by the so-called filtering method, wherein the transmitter 12 of the diagnostic ultrasound apparatus generates a normal drive signal without pulse inversion; and the sound-ray signal generator 14A/14C generates a sound ray signal for a B-mode image. Alternatively, other embodiments may be intended for fundamental imaging mode wherein the harmonic extraction process may not be performed.

The detailed configurations and operations of the components constituting the ultrasound diagnostic apparatuses 100A, 100B, 100C in the above embodiments can be appropriately modified without departing from the scope of the present invention.

What is claimed is:

1. A diagnostic ultrasound apparatus comprising:
   a sound ray signal generator that generates a sound ray signal based on a reception signal obtained from an ultrasound probe that transmits and receives ultrasound to and from a subject;
   an imaging signal generator that performs filtering of passing different bands on the sound ray signal to generate multiple imaging signals from the sound ray signal; and
   a calculator that performs a multiplication operation among the imaging signals, wherein the multiplication operation is a multiplication of brightness values of corresponding pixels at the same position in respective images that correspond to the imaging signals,
   wherein the calculator performs a power root calculation process on an arithmetically-processed imaging signal that is obtained by the multiplication operation among the imaging signals, the power root calculation process corresponding to the number of the imaging signals.

2. The diagnostic ultrasound apparatus according to claim 1, wherein the calculator performs a look up table conversion process on an arithmetically-processed imaging signal that is obtained by the multiplication operation among the imaging signals.

3. The diagnostic ultrasound apparatus according to claim 1, wherein a fractional bandwidth of −20 dB of the ultrasound probe is 100% or more.

4. The diagnostic ultrasound apparatus according to claim 1, further comprising a transmitter that generates a drive signal containing fundamentals of different frequencies and that outputs the generated drive signal to the ultrasound probe,
   wherein the sound ray generator generates the sound ray signal having harmonic components of the fundamentals.

5. The diagnostic ultrasound apparatus according to claim 1, wherein the calculator converts a brightness value of the imaging signals equal to or less than a certain value to zero before performing the multiplication operation.

6. The diagnostic ultrasound apparatus according to claim 1, further comprising a first display controller that displays a normal image and an arithmetically-processed image side by side simultaneously on a display, the normal image being based on a normal imaging signal on which the multiplication operation is not performed, the arithmetically-processed image being based on an arithmetically-processed imaging signal that is generated by the multiplication operation among the imaging signals.

7. The diagnostic ultrasound apparatus according to claim 1, further comprising:
   an analyzer that generates a difference image corresponding to a difference between a normal image and an arithmetically-processed image, the normal image being based on a normal imaging signal on which the multiplication operation is not performed, the arithmetically-processed image being based on an arithmetically-processed imaging signal that is generated by the multiplication operation among the imaging signals; and
   a second display controller that displays the difference image on a display.

8. The diagnostic ultrasound apparatus according to claim 7, wherein the second display controller colors the difference image and displays the colored difference image on the display.

9. The diagnostic ultrasound apparatus according to claim 7, wherein
   the analyzer calculates an index value based on the difference image, and
   the second display controller displays, on the display, the index value based on the difference image.

10. The diagnostic ultrasound apparatus according to claim 1, wherein the imaging signals are image data.

11. A non-transitory computer-readable storage medium storing a program that causes a computer to function as:
   a sound ray signal generator that generates a sound ray signal based on a reception signal obtained from an ultrasound probe that transmits and receives ultrasound to and from a subject;
   an imaging signal generator that performs filtering of passing different bands on the sound ray signal to generate multiple imaging signals from the sound ray signal; and
   a calculator that performs a multiplication operation among the imaging signals, wherein the multiplication operation is a multiplication of brightness values of corresponding pixels at the same position in respective images that correspond to the imaging signals, wherein the calculator performs a power root calculation process on an arithmetically-processed imaging signal that is obtained by the multiplication operation among the imaging signals, the power root calculation process corresponding to the number of the imaging signals.

\* \* \* \* \*